(12) United States Patent
Shivapuja et al.

(10) Patent No.: US 10,179,035 B2
(45) Date of Patent: Jan. 15, 2019

(54) DIRECT 3D-PRINTED ORTHODONTIC ALIGNERS WITH TORQUE, ROTATION, AND FULL CONTROL ANCHORS

(71) Applicant: Real 3D Polymers, LLC, Troy, MI (US)

(72) Inventors: Prasanna-Kumar Shivapuja, Roseville, MI (US); Dinesh Shah, Troy, MI (US); Nidhi Shah, Chicago, IL (US); Sureshkumar Shah, Troy, MI (US)

(73) Assignee: Real 3D Polymers Group LLC, Troy, MI (US)

( * ) Notice: Subject to any disclaimer, the term of this patent is extended or adjusted under 35 U.S.C. 154(b) by 0 days.

(21) Appl. No.: 15/062,043

(22) Filed: Mar. 4, 2016

(65) Prior Publication Data

US 2016/0256240 A1 Sep. 8, 2016

Related U.S. Application Data

(60) Provisional application No. 62/128,450, filed on Mar. 4, 2015.

(51) Int. Cl.
*A61C 3/00* (2006.01)
*A61C 7/08* (2006.01)
*A61C 13/00* (2006.01)
*B33Y 50/02* (2015.01)

(52) U.S. Cl.
CPC ............ *A61C 7/08* (2013.01); *A61C 13/0013* (2013.01); *B33Y 50/02* (2014.12)

(58) Field of Classification Search
CPC ........ A61C 7/08; A61C 13/0013; B33Y 50/02
See application file for complete search history.

(56) References Cited

U.S. PATENT DOCUMENTS

| 9,757,211 | B2 * | 9/2017 | Ward | A61C 7/146 |
|---|---|---|---|---|
| 9,795,460 | B2 * | 10/2017 | Martz | A61C 7/08 |
| 2005/0048433 | A1 * | 3/2005 | Hilliard | A61C 7/00 433/24 |
| 2008/0182218 | A1 * | 7/2008 | Chen | A61C 7/00 433/6 |
| 2008/0227047 | A1 * | 9/2008 | Lowe | A61C 7/00 433/2 |

(Continued)

*Primary Examiner* — Nicholas Lucchesi
(74) *Attorney, Agent, or Firm* — Timberline Patent Law Group PLLC; Mark Farrell

(57) ABSTRACT

Direct 3D-printed orthodontic aligners with torque, rotation, and full-control anchors are provided. In an implementation, an orthodontic system uses 3D-printed aligners to perform orthodontic treatment of teeth. Manufacturing the aligners by 3D-printing or additive manufacturing processes imparts novel geometries to the aligners for applying torque, rotation, and full 3D control forces to the teeth in novel ways. The 3D-printed aligners may contain multiple different plastic or metal materials with different orthodontic properties. In an implementation, divot anchors can be strategically applied to teeth to work in conjunction with a 3D-printed aligner fitted over the divot anchors and teeth. The divot anchors may include a depression, channel, groove, or notch providing an attachment point for the aligner to apply a force to the tooth through the divot anchor, such as a torque, rotational force, leverage, push, pull, or 3D control force.

16 Claims, 36 Drawing Sheets

(56) References Cited

U.S. PATENT DOCUMENTS

| | | | |
|---|---|---|---|
| 2009/0148803 A1* | 6/2009 | Kuo | A61C 7/08 433/7 |
| 2011/0020761 A1* | 1/2011 | Kalili | A61C 7/08 433/6 |
| 2013/0095446 A1* | 4/2013 | Andreiko | A61C 7/08 433/6 |
| 2013/0122448 A1* | 5/2013 | Kitching | A61C 7/002 433/24 |
| 2013/0323665 A1* | 12/2013 | Dinh | A61C 7/08 433/6 |
| 2014/0072926 A1* | 3/2014 | Valoir | A61C 7/08 433/6 |
| 2015/0157421 A1* | 6/2015 | Martz | A61C 7/08 433/6 |
| 2015/0238283 A1* | 8/2015 | Tanugula | A61C 7/002 433/6 |
| 2016/0051341 A1* | 2/2016 | Webber | A61C 7/12 433/6 |
| 2016/0193014 A1* | 7/2016 | Morton | A61C 7/08 433/6 |
| 2017/0135793 A1* | 5/2017 | Webber | A61B 1/0002 |
| 2018/0000563 A1* | 1/2018 | Shanjani | A61C 7/002 |
| 2018/0000565 A1* | 1/2018 | Shanjani | A61C 7/08 |

* cited by examiner

1301

1302

1303

1401

1402

1403

1701

1702

1703

1704

DIRECT 3D-PRINTED ORTHODONTIC ALIGNERS WITH TORQUE, ROTATION, AND FULL CONTROL ANCHORS

RELATED APPLICATIONS

This nonprovisional patent application claims the benefit of priority to U.S. Provisional Patent Application No. 62/128,450 to Shivapuja et al., filed Mar. 4, 2015, and incorporated herein by reference in its entirety.

TECHNOLOGY FIELD

The subject matter is directed to orthodontia, and specifically to 3D printing technologies applied to direct manufacture of orthodontic aligners for straightening teeth with innovative anchors to be placed on the teeth in conjunction with the aligners. The subject matter is also directed to aligner designs, and materials to be used in additive manufacturing processes for making the aligners and anchors.

BACKGROUND

Currently, there are two main systems in the market for correcting the position of teeth. The first system is a braces scenario that may include traditional self-ligating orthodontic brackets with a steel tight bracket, a straight wire application, or a traditional Tweed appliance. The second system is a clear aligner system, in which aligners are interchangeable by the patient during treatment. The clinician may prescribe a series of aligners, which are generally placed over, but are not themselves adhesively secured or otherwise attached to, the patient's teeth, to move one or more teeth from their original position to their aesthetically pleasing or functionally corrected position. Typically, a series of aligners is required to fully treat the patient because the degree of movement produced by a given single aligner is limited. One such aligner system is the INVISALIGN aligner system (Align Technology, Inc., San Jose, Calif.). Each aligner is responsible for moving the teeth toward their final pre-determined or aesthetically/functionally correct position.

The INVISALIGN aligners are fabricated by physical and computer-aided molding processes. The conventional process begins by taking an impression of the patent's dentition, or using intra-oral scanner for teeth impression, followed by creating a denture model of the teeth on computer. This CAD file, for example an .STL file, is used to 3D-print the physical teeth models and molds. Finally, clear plastic which will form the aligner, such as a polyurethane, is molded (e.g., thermoformed) over the physical teeth model or mold of the tooth configuration to be implemented. Subsequent physical steps of the conventional process trim the molded aligner to remove sharp edges or portions which might contact and irritate the gingiva. In addition, the aligner surface and edges are typically smoothed via a process such as tumbling.

This conventional fabrication of aligners is a tedious process, which compounds both cost and time of treatment for the patient. Since such an orthodontic treatment may require, for example, 25 intermediate reset molds to represent 25 stages of treatment progress, the cost and time required for the necessary steps of mold making, aligner formation, and trimming, may be prohibitively high. The cost is additive, as each new stage in treatment or each change in treatment requires the production of a new mold. Likewise, the cost of storing a series of molds for each patient throughout treatment may be formidable. U.S. Pat. No. 5,975,893 to Align Technologies, Inc., is incorporated by reference herein in its entirety, to describe the processes elaborated above, as background information.

Treatment of malocclusion by aligners faces challenges other than the difficulty of manufacture. Specifically, aligners fastened with attachments may prove very difficult to install, as a result of the limited number of shapes that the attachment apertures on the aligner may take, consistent with the INVISALIGN manufacturing process. Specifically, the attachment apertures are formed by thermoforming over a stereolithographically-generated positive tooth model, which limits the type of apertures that may be made. Moreover, aligners may bind with the attachments and prove very difficult to remove. Furthermore, in many aligner patients, the presence of the aligner within the patient's mouth causes a change in the points of occlusion between the mandible and maxilla, and in particular, causes the guidance of occlusion to move to the rear molars. This opens the patient's bite and typically intrudes the rear molars as a consequence of the unbalanced occlusion force on the rear molars.

One result of this conventional unbalanced occlusion force can be TMJ injury after the removal of the aligner, because the force of the mandible is no longer resisted by the rear molars in the absence of the aligners. For many patients aligners fabricated manually or by thermoforming on a positive model are uncomfortable and can irritate the patient's gingiva and/or tongue to such an extent that the soft tissue becomes inflamed and can potentially bleed. This discomfort is generally caused because the aligner is trimmed inaccurately to the patient's gingival margin. The inaccuracy in trimming is generally caused by the minimum size of the trimming tool particularly on the anterior lingual side where the aligner interferes with the tongue. Other anatomy such as the incisive papilla, if not generally considered when trimming the aligner, can cause swelling or inflammation. In addition, the location where the aligner is trimmed can cause a sharp flange to be created at the base of the aligner near the gingival margin, particularly on the lingual side.

Due to disadvantages of thermoforming and to reduce the steps involved in conventional aligner manufacturing methods, as well as aligner design limitation of thermoforming process, an alternative method is needed to manufacture an aligner to configure better to the counters of the teeth and to provide better finishing of the appliance. This would reduce the inaccuracy of each step to provide better adaptation, better fit, and better finish.

An ideal alternative apparatus and methodology for realizing aligners configured to correspond to a series tooth configurations should be economical, reusable, reduce time consumption, reduce material waste, and in particular, should reduce the need for fabricating multiple casts of teeth arrangements for various stages in the orthodontic treatment.

SUMMARY

Direct 3D-printed orthodontic aligners with torque, rotation, and full-control anchors are provided. In an implementation, an orthodontic system uses 3D-printed aligners to perform orthodontic treatment of teeth. Manufacturing the aligners by 3D-printing or additive manufacturing processes imparts novel geometries to the aligners for applying torque, rotation, and full 3D control forces to the teeth in novel ways. The 3D-printed aligners may contain multiple different plastic or metal materials with different orthodontic properties. In an implementation, divot anchors can be strategically applied to teeth to work in conjunction with a 3D-printed aligner fitted over the divot anchors and teeth. The divot anchors may include a depression, channel, groove, or notch providing an attachment point for the aligner to apply a force to the tooth through the divot anchor, such as a torque, rotational force, leverage, push, pull, or 3D control force.

An example system overcomes the drawbacks of current manufacturing methods for aligners. The example system also overcomes disadvantages of current aligner appliances for torqueing the teeth and applying rotation control to the teeth.

An example process achieves direct 3D printing of orthodontic aligners (additive manufacturing of aligners) and uses innovative anchoring designs. Special orthodontic materials are also developed for 3D printing processes.

An example process can direct 3D-print thin, variable thickness, and hard (or hard/soft) aligners, and aligners with different properties at different locations, in a single processing step using one or combination of 3D-printing processes. The 3D-printing processes may be a FDM (fused deposition modeling) process, a SLS (selective laser sintering) process, a SLM (selective laser melting) process, a direct pellets fused deposition process, a SLA (stereolithography) process, a multi-jet photo cured polymer process, an HP Multi Jet Fusion technology process, and a continuous liquid interface production technology (CLIP) process, which uses a tunable photochemical process instead of a conventional mechanical approach to eliminate shortcomings of conventional layer-by-layer 3D-printing technology, to rapidly transform 3D models into final parts in a range of engineering-grade materials. Several other additive manufacturing processes may also be used.

Example aligner designs are presented, including anchoring designs to be used with the aligners in order to apply force to teeth at pre-determined positions on the teeth. The example anchor designs allow for precise force delivery to increase the efficiency of moving a tooth to a predetermined positions computed by computer software. In an implementation, an anchoring device is referred to as a "divot anchor" because of its shape, which provides a divot or depression which the aligner can removably attach onto to apply a force to the tooth. Example divot anchor designs are smoother to tongue and cheek, provide a more precise area for force application, since the anchor is flatter that conventional devices, can be placed in areas where there is less space, and on anterior teeth the anchor can be made into a rectangle simulating the bracket slot of a conventional orthodontic bracket. Forces applied by the aligner can be exerted by a soft material engaging into the rectangular anchor, which can be molded to the contours by the 3D-printed dual material aligner system.

This summary is not intended to identify key or essential features of the claimed subject matter, nor is it intended to be used as an aid in limiting the scope of the claimed subject matter.

DETAILED DESCRIPTION

Overview

Figure 1:
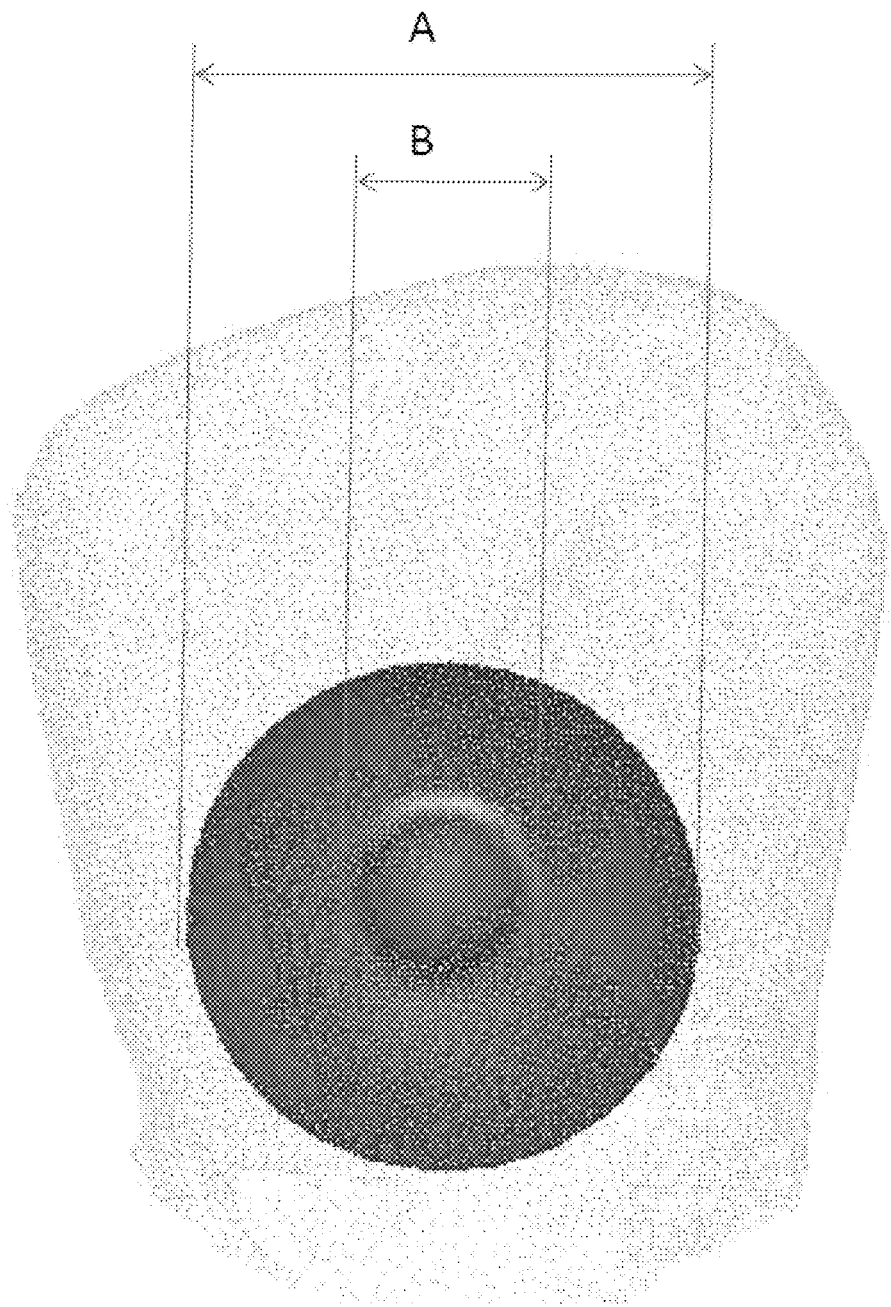
FIG. 1 is a diagram of an example divot anchor and a top view as mounted on teeth.

This disclosure describes direct 3D-printed orthodontic aligners with example torque, rotation, and full-control anchors, including systems, methods, and materials for manufacturing 3D-printed orthodontic appliances such as aligners, and also anchors, including novel "orthodontic divot anchors" (hereinafter, "divot anchors"). An example system can use divot anchors for correcting the rotation and torque control of anterior teeth, and for three-dimensional control of teeth in general.

An example process applies direct 3D-printing or additive manufacturing to create aligners and divot anchors that apply the design and mechanics concepts described herein. Example 3D-printing processes use medical-grade and medically approved materials, for example 3D-printable materials that are elastic in nature, to exert comfortable forces when a patient wears the 3D-printed aligners. Upon exertion of force, an example aligner may extend or stretch but then returns to original position to exert constant force, assisting in the programmatic movement of teeth. An example 3D-printing process prints thin, variable-thickness, hard, and hard-soft aligners, as well as aligners that may have different properties at different places or sections on the aligner, 3D-printing, for example, in a single step using an FDM process, an SLS process, a direct pellets fused deposition process, SLA, multi-jet photo cured polymer processes, HP Multi Jet Fusion technology, continuous liquid interface production technology (CLIP), and other 3D-printing processes.

The example systems and processes described herein provide unique anchoring designs on teeth, which work in conjunction with aligners and other hardware for improved tooth movement with less discomfort, reduced time of treatment, and easy placement and removal of the 3D-printed aligners and devices.

Example Systems

The following paragraphs describes various embodiments of the subject matter. The subject matter is not intended to be limited by specific examples, and those skilled in the art can apply the principles described in ways not specifically disclosed, while remaining within the scope of the subject matter described.

In an implementation, an example system provides new orthodontic anchors, referred to herein as "divot anchors" for correcting the rotation and torque control of anterior teeth, and also three-dimensional control of teeth in general. The example divot anchors and 3D-printed aligners work in cooperation with each other to provide better and faster orthodontic realignment of teeth.

Example systems that directly 3D-print aligners and divot anchors use medically approved, orthodontic grade materials having, for example, elasticity by nature. These can exert comfortable force when worn by the patient. Upon exertion of a force the aligner may extend or stretch but returns to its original position to exert a constant force for effecting programmed teeth movement.

FIGS. 1-5 show example designs of divot anchors, including some spatial dimensions. FIGS. 6-12 show application of novel concepts as explained in context of the principles of Andrews' straight-wire appliance approach. These can provide three-dimensional control of teeth (i.e., straitening the teeth) with a removable, directly 3D-printed, series of plastic aligners (i.e., a series of aligners printed by additive manufacturing) utilizing anchor points and example divot anchors as described. FIGS. 13-17 show dynamics of example anchor geometry and placement.

FIGS. 18-29 show example concepts and dynamics of correcting rotation of teeth. Three example concepts are shown, including applying an innovative divot anchor with spacer to reduce resistance in an opposing direction, achieving rotation to create a couple with divot anchor, spacer, and soft reline, and using a suction cup with two divot anchors diagonally opposite on the tooth. FIGS. 30-36 show innovative design concepts for torque control of anterior teeth, with proposed improvements to create engagement of the aligner at the point of application of force, by making the aligner engage into the divot anchor on the buccal side towards the gingival margin, while creating spaces on the opposite side to reduce resistance.

Example Divot Anchors

FIG. 1 shows an example divot anchor and top view as mounted on teeth. Dimension A is the width of the divot anchor, which is, for example, ⅔ of the width of the tooth. Dimension B is the width between two vertical peaks of elevation of the divot anchor, to be shown in next Figures.

Figure 2:
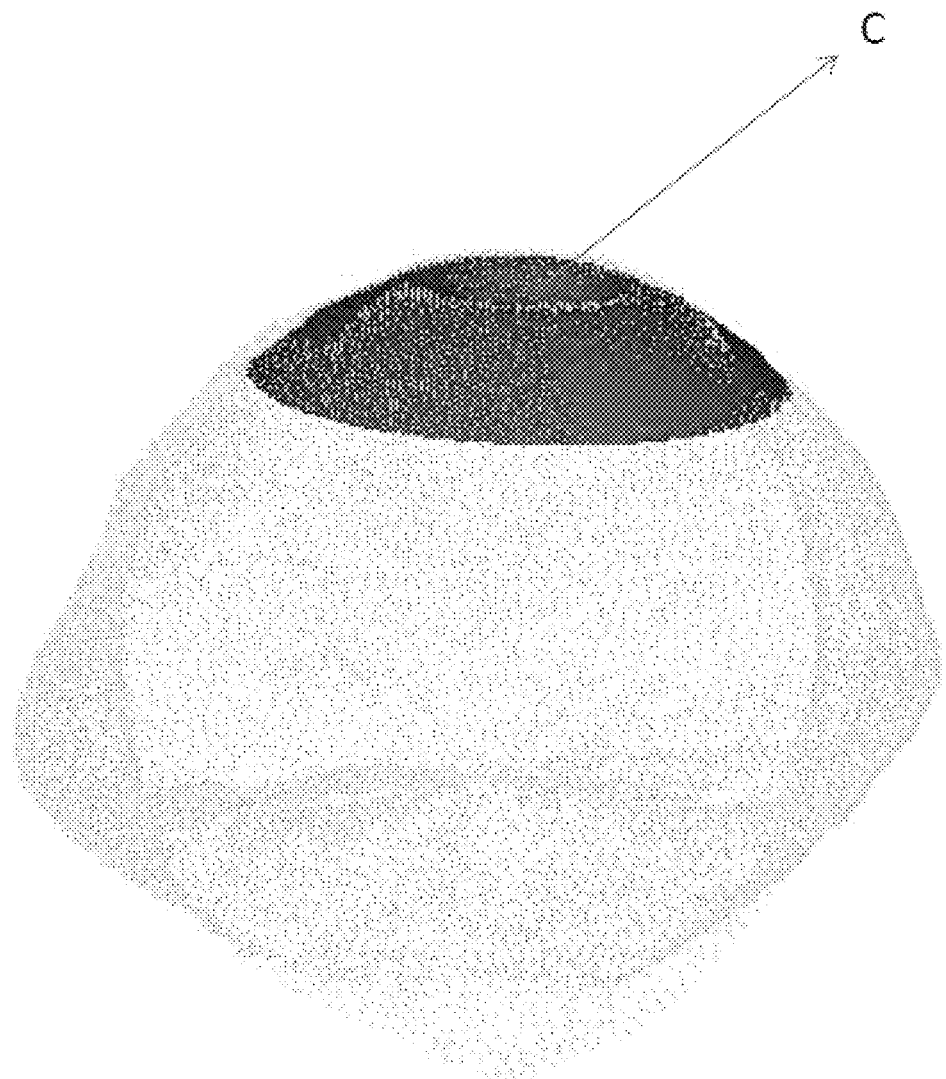
FIG. 2 is a diagram of a second view of the example divot anchor, showing an example depression in the divot anchor.

FIG. 2 shows another view of the example divot anchor, showing the divot, or depression. Dimension C is the depth of the valley, divot, or depression.

Figure 3:
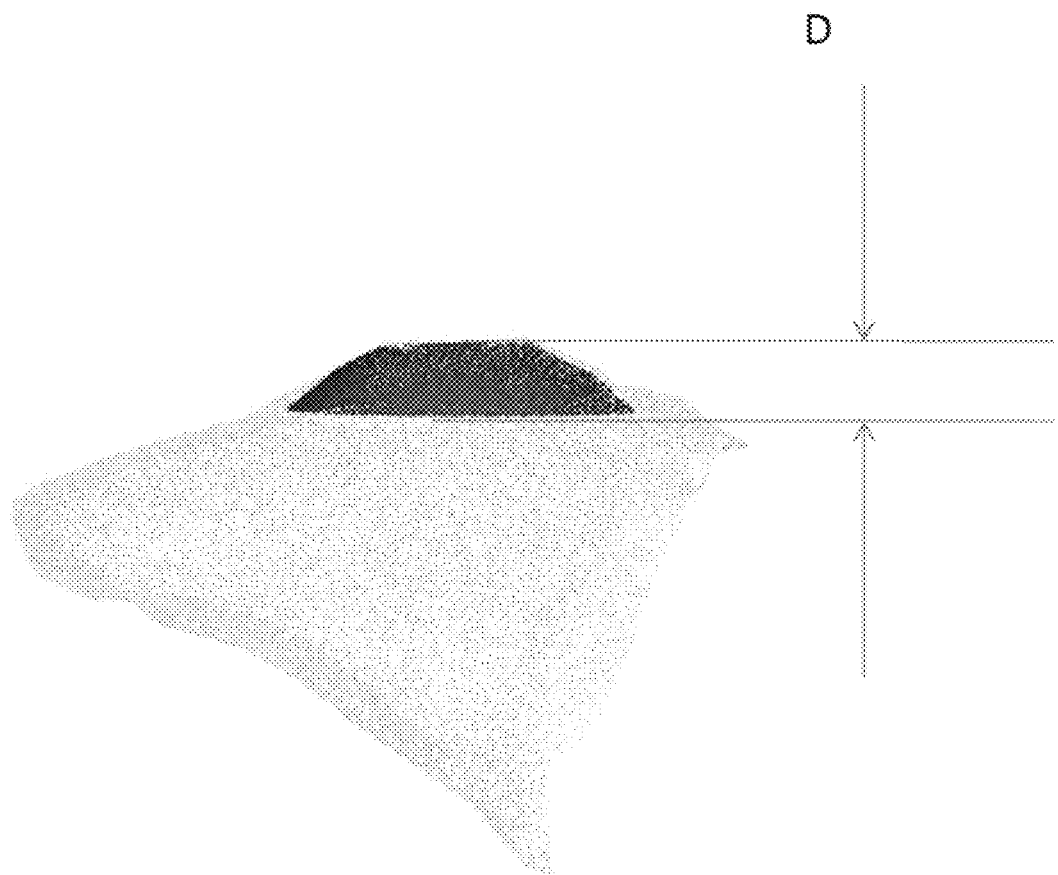
FIG. 3 is a diagram of another view of the example divot anchor, showing the height, for example.

FIG. 3 shows another view of the example divot anchor, showing dimension D, the height. An example 3D-printer aligner can fit on top of the divot anchor, and the divot, depression, or valley can be completely filled with plastic of the aligner. By contrast, it is not possible to make a conventional INVISALIGN or other thermoformed aligner fit into to such a depression or valley of the example divot anchor, as it is not possible to make a thermoformed aligner with predefined variable thicknesses (that is, predefined thick and thin sections) within the same aligner. But 3D-printing allows a manufacture of this kind, with divot anchors and matching aligners that take advantage of the divots for force leverage.

Figure 4:
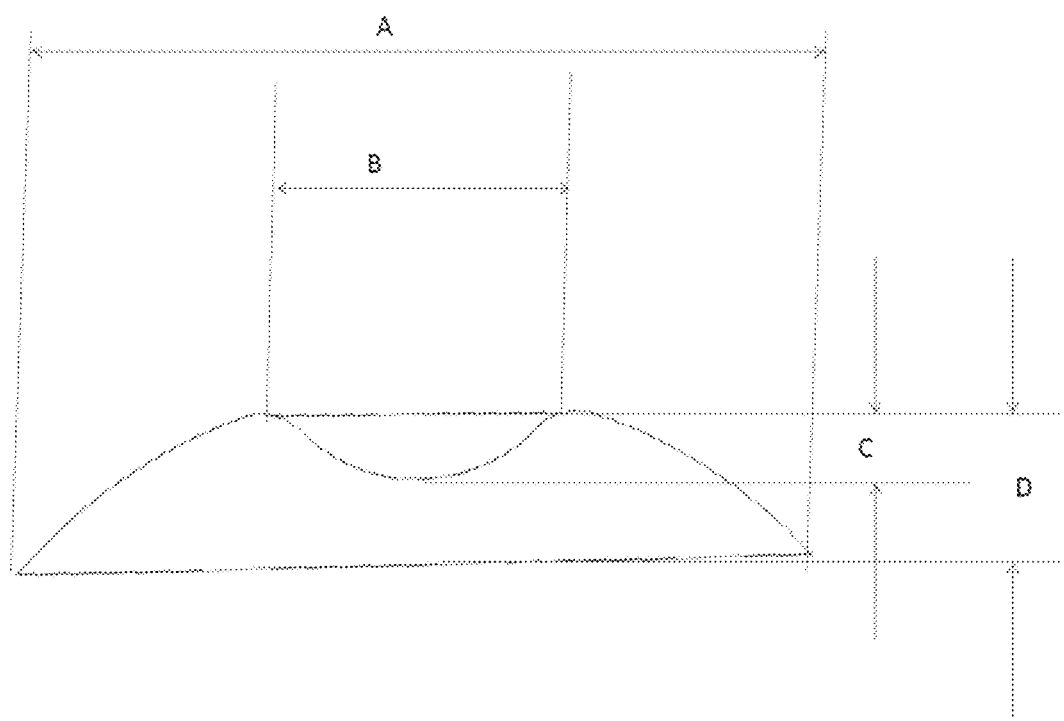
FIG. 4 is a diagram showing a two-dimensional cross section of the example divot anchor.

FIG. 4 shows a two-dimensional cross section of the example divot anchor. Dimension A is the width of the divot anchor, which in this case is ⅔ of the width of the tooth. Dimension B is the distance between the two peaks of elevation on either side of the divot, or depression. Dimension C is the depth of the divot, valley, or depression. The ratio of A/B can vary from 5 to 2, while the ratio of B/C can vary from 8 to 3. The ratio of C/D can vary from 0.2 to 1.0.

Figure 5:
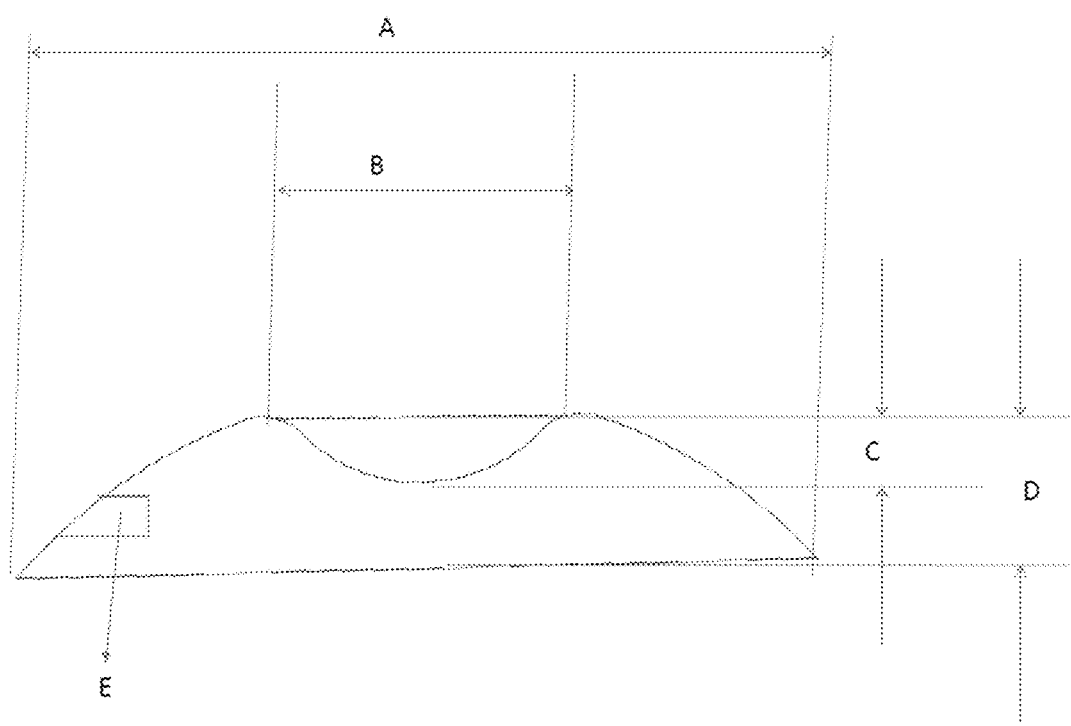
FIG. 5 is a diagram of an example divot anchor, showing a notch or channel for engaging an aligner and more anchoring design parameters for torque control and application of forces to a tooth.

FIG. 5 shows more example anchoring system designs of the divot anchor. In an implementation, the example divot anchor has a circular groove E as shown. In one embodiment, a hook design may also be incorporated into an aligner, which can be attached on the divot anchor to deliver force more effectively to where the force is needed on the teeth. Such is not feasible with current plastic aligners made by thermoforming or other conventional processes. Only 3D-printing allows the manufacture this such designs shown in FIG. 5.

Figure 6:
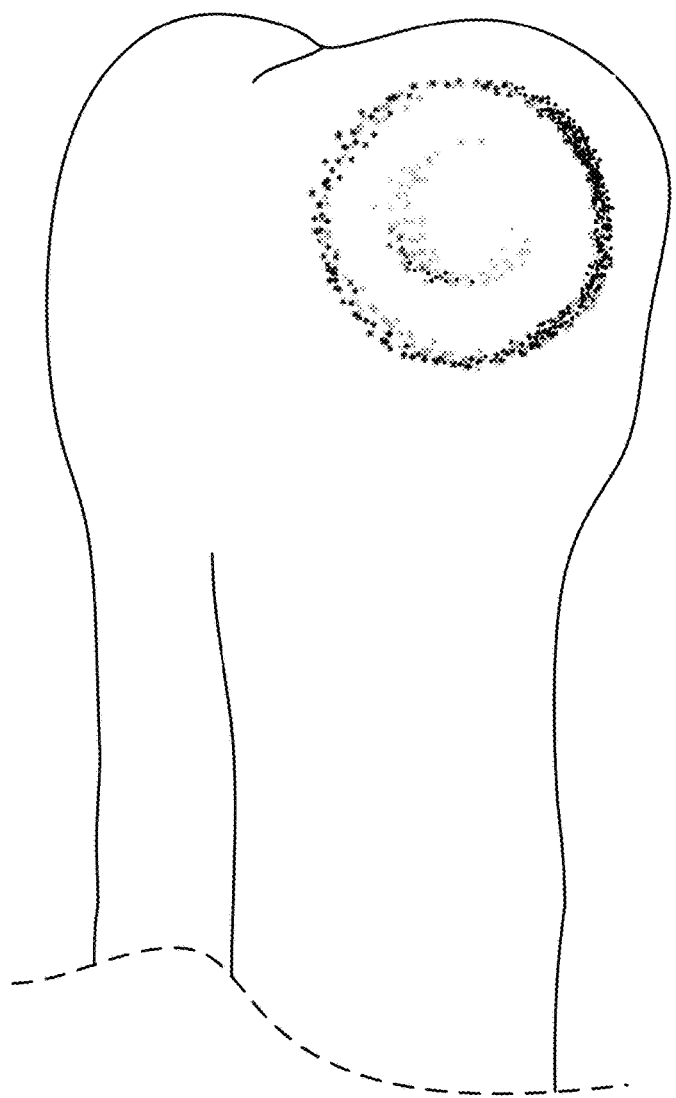
FIG. 6 is a diagram showing an example divot anchoring design mounted on single tooth for rotation control.

FIG. 6 shows an example divot anchoring design mounted on single tooth for rotation control.

Figure 7:
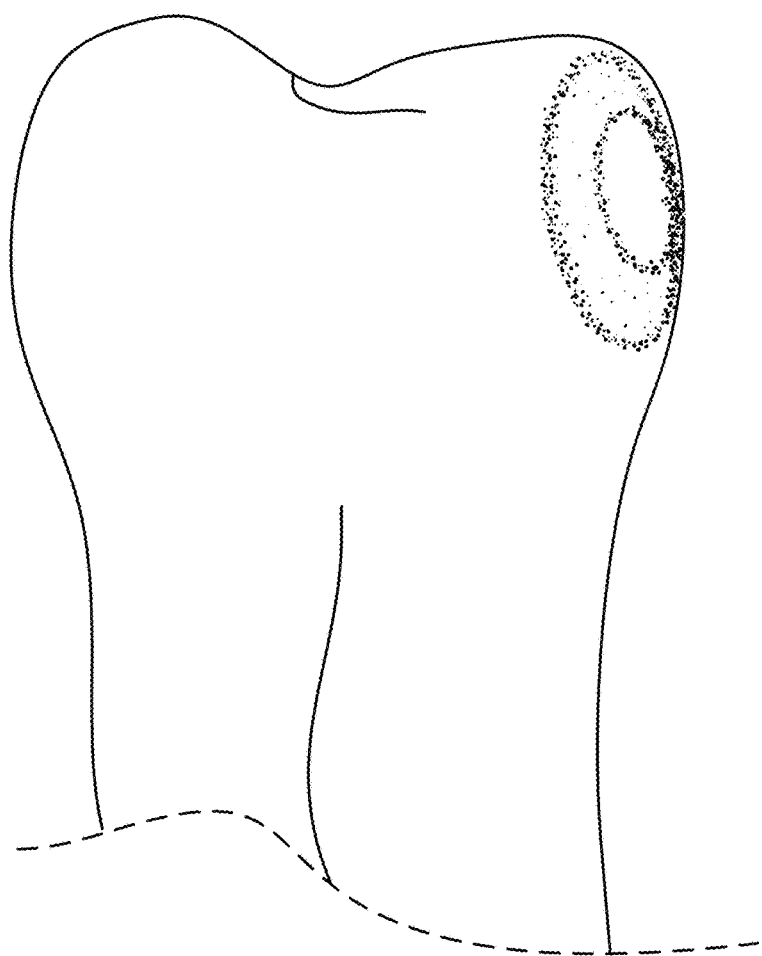
FIG. 7 is a diagram showing the example divot anchoring design of FIG. 6 from a different angle and view.

FIG. 7 shows then example divot anchoring design of FIG. 6 mounted on single tooth for rotation control, at different angle or view.

Figure 8:
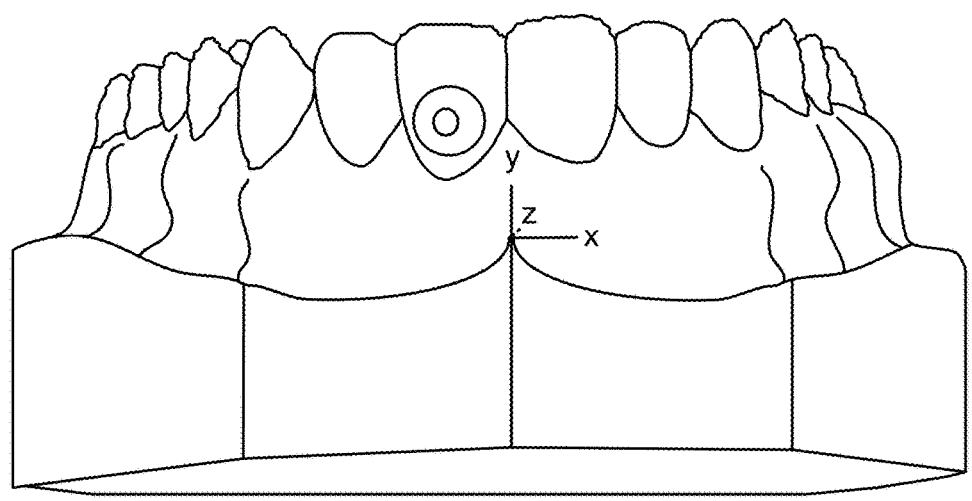
FIG. 8 is a diagram showing an example divot anchoring design mounted on single tooth for rotation control, in relation to an ideal teeth model.

FIG. 8 shows the example divot anchoring design mounted on single tooth for rotation control, shown in relation to the ideal teeth of an ideal dental model.

Figure 9:
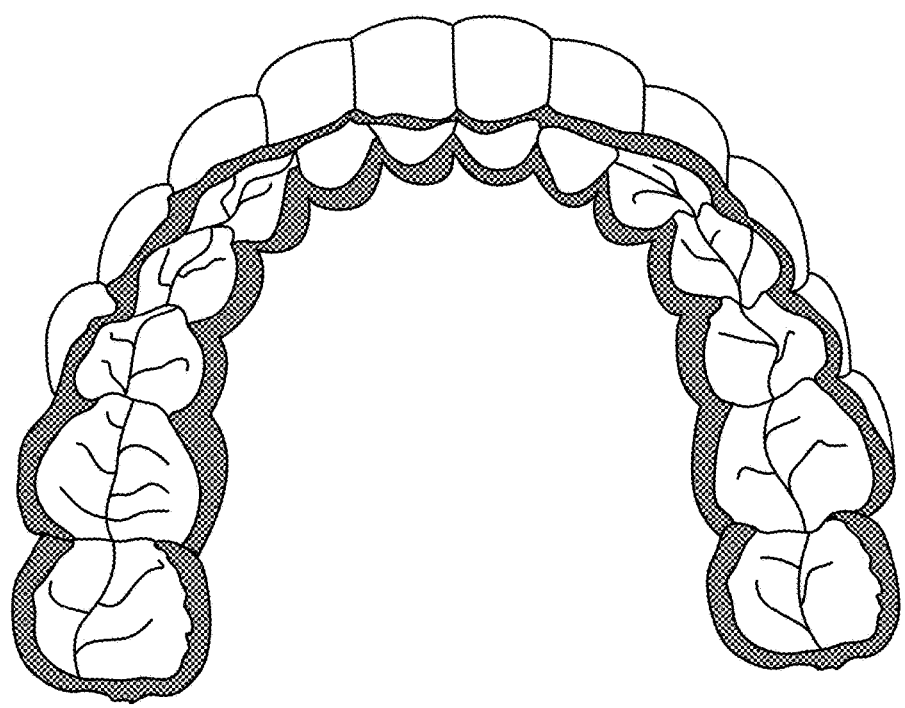
FIG. 9 is a diagram showing an example CAD file model of a 3D-printed aligner.

FIG. 9 shows a shows a CAD design of an example 3D-printed aligner model.

Figure 10:
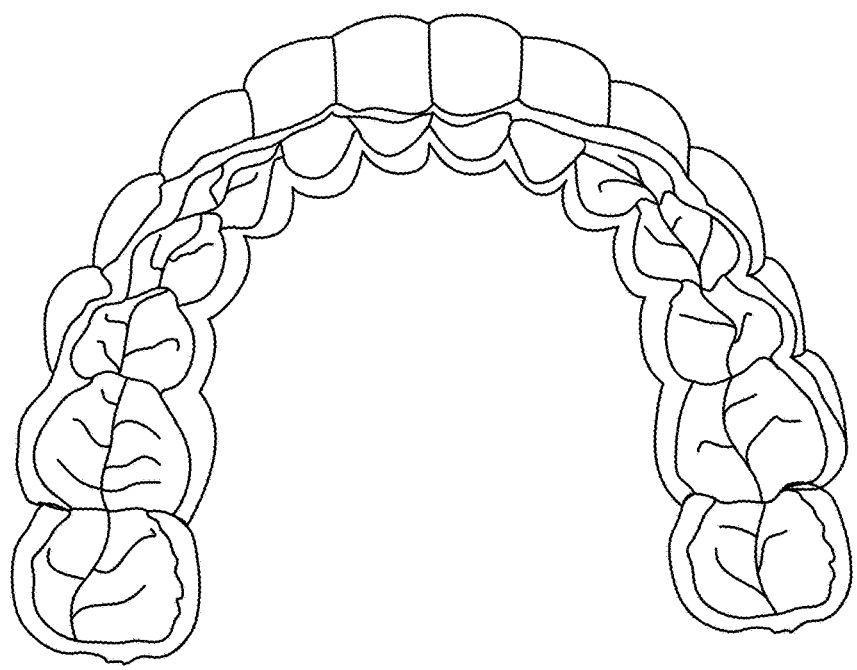
FIG. 10 is a diagram showing an example actual 3D-printed aligner, based on the generated CAD model of FIG. 9.

FIG. 10 shows an actual 3D-printed aligner manufactured from the CAD design of FIG. 9.

Figure 11:
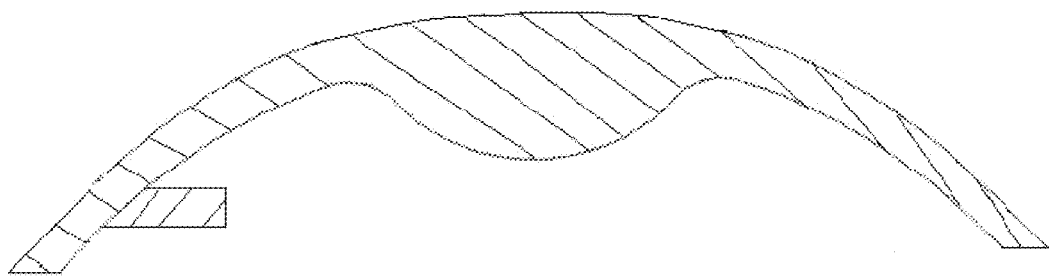
FIG. 11 is a diagram showing an example cross section of another design of an example aligner where the aligner fits into a groove of the divot anchor, and in which the aligner has a rib design or circular groove that is not possible to make by conventional thermoforming aligner manufacturing methods.

FIG. 11 shows a cross-section of an example aligner that has a piece, member, rib, or tab that fits into groove of the divot anchor, such as groove E in FIG. 5. The example aligner may have a rib design or a circular groove, which is not possible to manufacture by conventional thermoforming or conventional CAD/CAM methods. Only 3D-printing allows manufacture of the example aligners.

Figure 12:
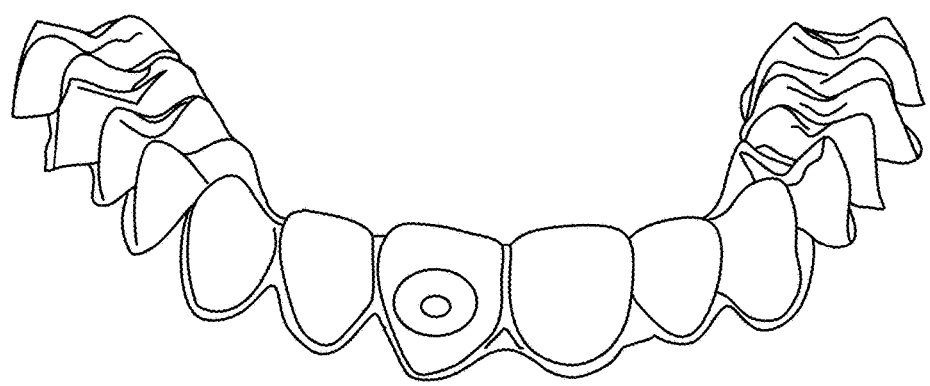
FIG. 12 is a diagram showing an example aligner appliance for use with the example divot anchor as mounted on a tooth.

FIG. 12 shows an example aligner for use in conjunction with an example divot anchor mounted on a tooth, such as that shown in FIG. 8.

Example Full Control Anchors

Example anchors can provide three-dimensional control for realignment of misaligned teeth. Current conventional designs of the INVISALIGN aligner cannot have three-dimensional control of the teeth due to their manufacturing methods and design limitations.

In an implementation, an example aligner is based on principles of the Andrews' straight-wire appliance. The principles provide three-dimensional control of misaligned teeth (straitening the teeth) with removable, directly 3D-printed (additive manufactured) plastic aligners utilizing anchor points as described below. The benefits compared with conventional braces with wires are: easily removal, ease of cleaning, more predictable alignment, and easier tasking by the orthodontist.

Figure 13:
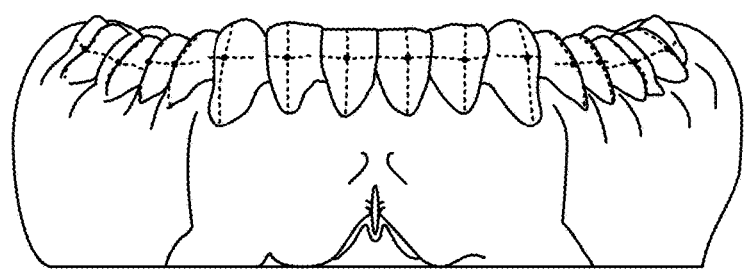
FIG. 13 is a diagram showing example front, left, and right views of an example reference point on each tooth, on the buccal or lingual surface, which when aligned makes the teeth come into alignment in three dimensional space, the reference point being referred to as a FA (Facial Axial) point.
Figure 13:
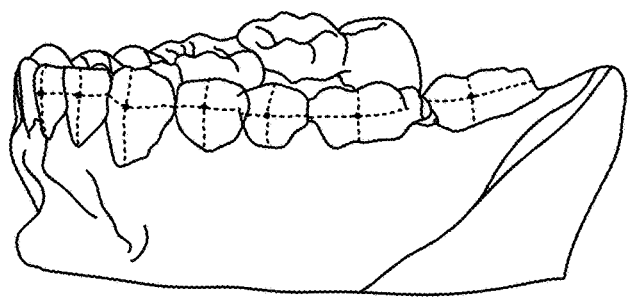
Figure 13:
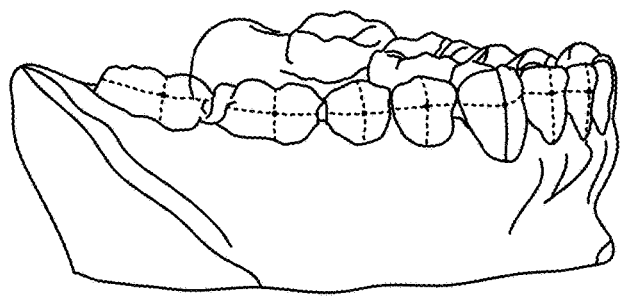

In an implementation, each tooth has a specific position in the arch and a relative position to the neighboring teeth. Each tooth can have a reference point on it, on the buccal or lingual surface, and when aligned makes the teeth come into alignment in three-dimensional space. This point is referred to as FA (Facial Axial) point by Dr. Andrews, as shown in FIG. 13 FIG. 13 shows the FA point view from front 1301, left 1302, and right 1303. These can be the primary reference points for placing the example anchors. The anchors are placed on this point or equidistance from this point either occlusal, gingival mesial, or distal on each tooth.

Figure 14:
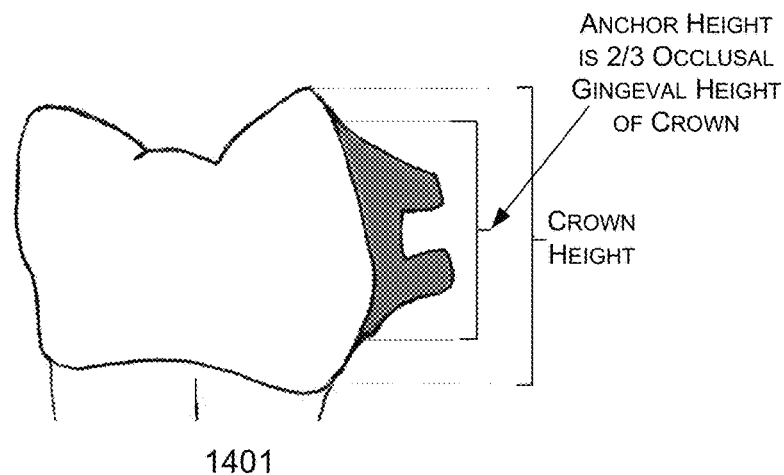
FIG. 14 is a diagram showing example anchor height, anchor slot height, and anchor slot depth parameters for example anchors for an example plastic aligner to fit onto.
Figure 14:
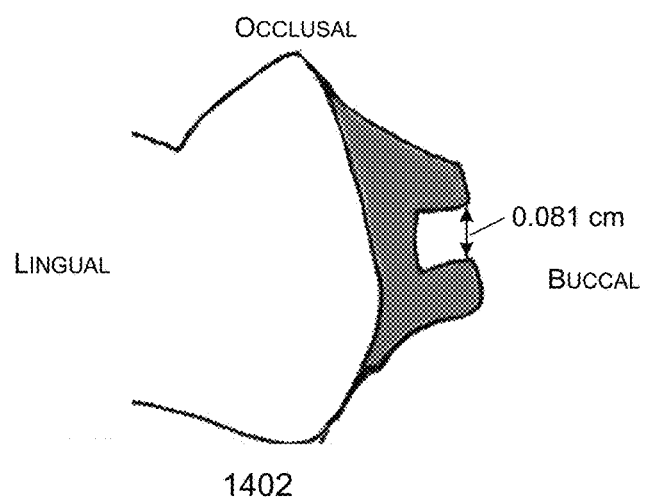
Figure 14:
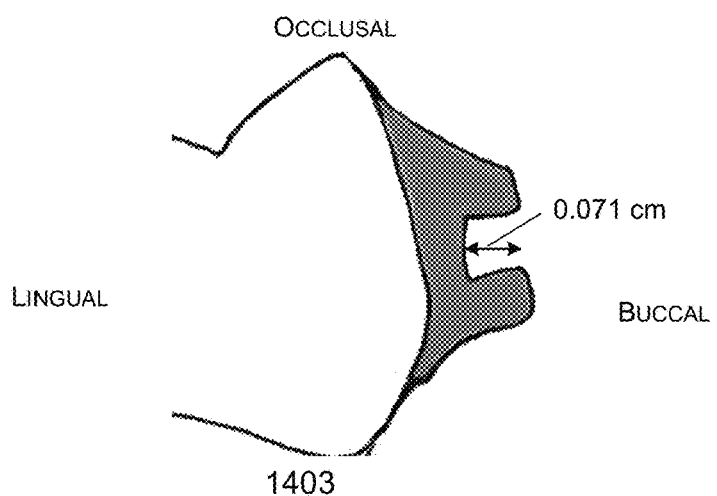

FIG. 14 shows dimensions of an anchor, such as the anchor height 1401, anchor slot height 1402, and anchor slot depth 1403. The plastic aligner fits onto these anchors. Such aligner design is not feasible with current plastic aligners made by thermoforming or other conventional processes.

Only 3D-printing allows the manufacture of such designs as shown in FIG. 14. In an implementation, the anchor height is ⅔ the occlusal gingival height 1401. The anchor slot height 1402 may be 0.81 cm. The anchor slot depth 1403 may be 0.71 cm.

Figure 15:
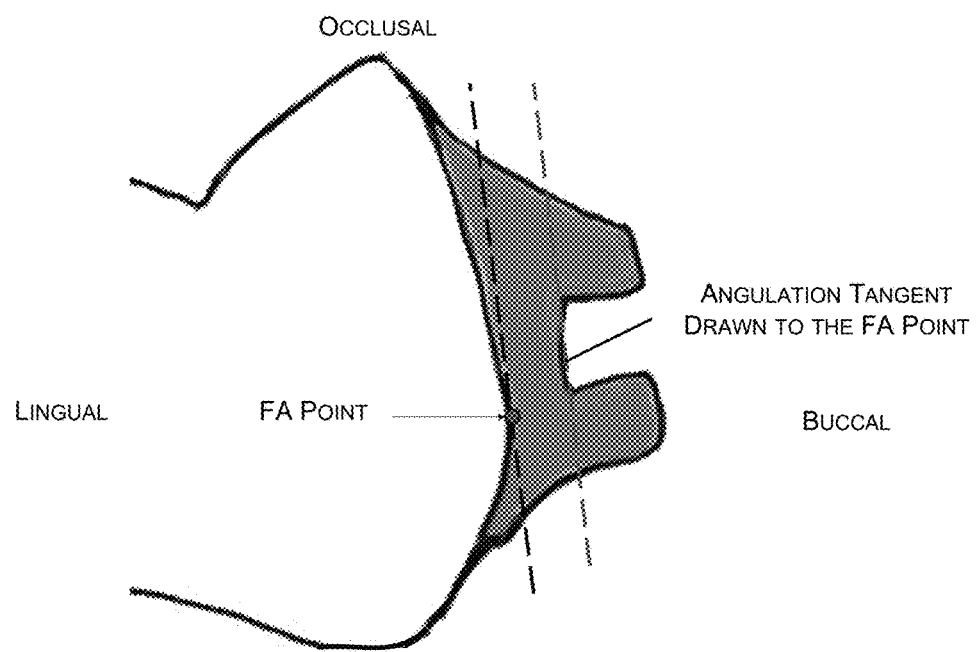
FIG. 15 is a diagram showing an example anchor slot angulation parallel to a tangent drawn on the buccal surface passing thru an FA Point introduced with respect to FIG. 13.

FIG. 15 shows anchor slot angulation: parallel to a tangent drawn on the buccal surface passing thru the FA point.

Figure 16:
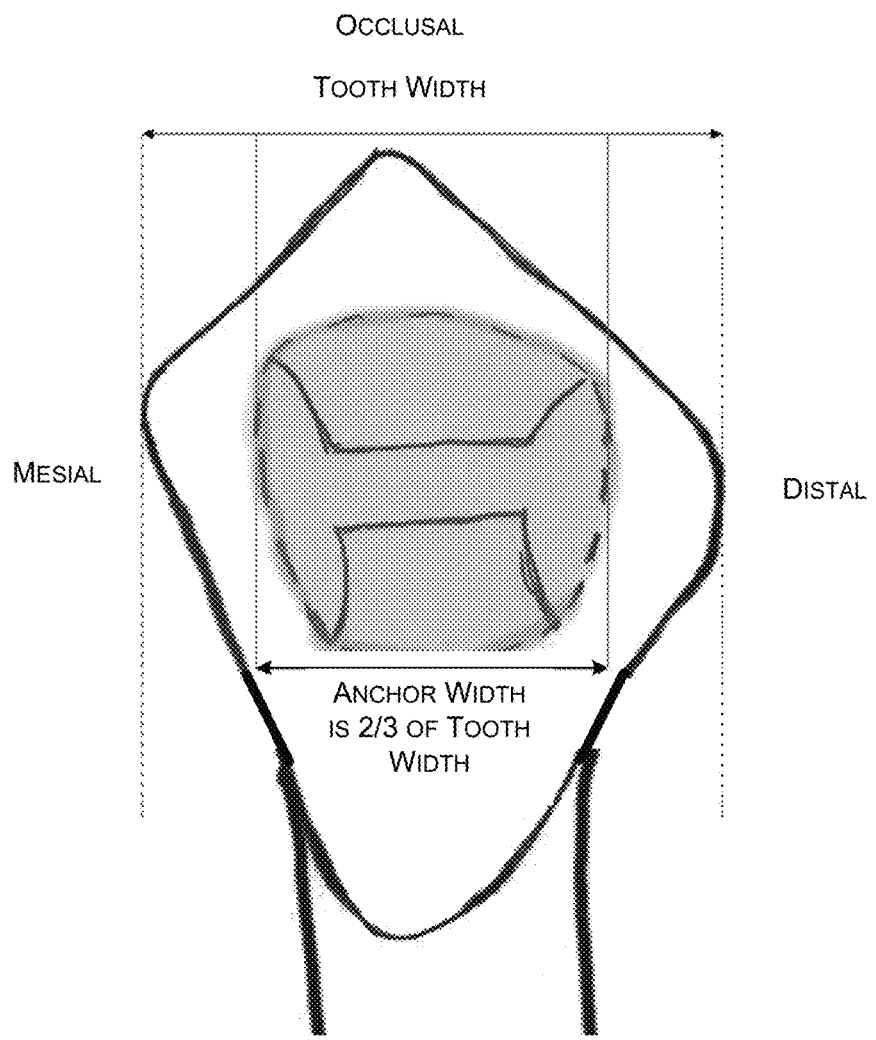
FIG. 16 is a diagram showing an example width of an example anchor, which is, for example, ⅔ the size of the tooth, with the center of the arches placed to the center of the tooth mesiodistally.

FIG. 16 shows an example width of the anchor which can be ⅔ the size of the tooth with the center of the arches placed on the center of the tooth mesiodistally.

Figure 17:
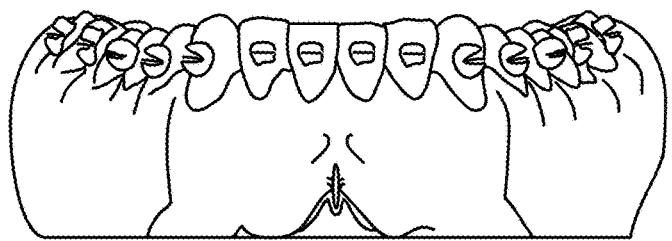
FIG. 17 is a diagram showing example shows 3D models with anchors placed on them to show how appearance from front, left, right and top.
Figure 17:
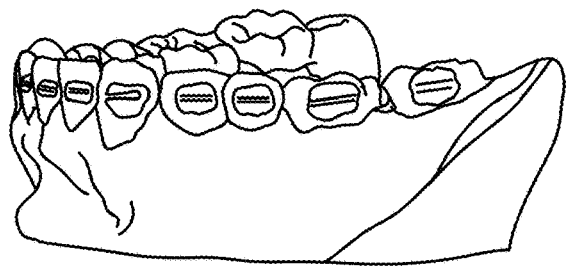
Figure 17:
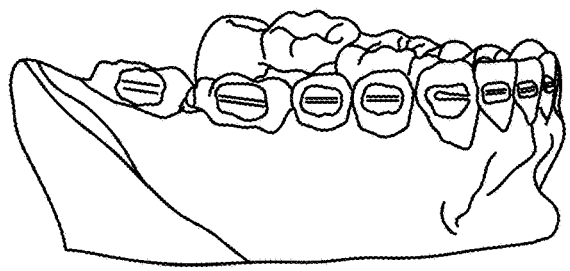
Figure 17:
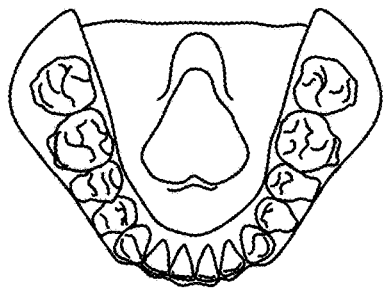

FIG. 17 shows three-dimensional models with anchors placed to show an appearance from the front 1701, the left 1702, the right 1703, and the top 1704.

In an implementation, the following are steps for placing anchors on teeth:

1. First align the teeth digitally to their final position in a computer model or virtual model.

2. Calculate anchor points to be placed on each tooth or necessary teeth to be moved at the predetermined point FA point or a point in relation to this point consistent on all the teeth, digitally.

3. Determine each anchor point to have a movement prescription in angulation, rotation, and torque and a buccolingual position built into it, as determined by final position of teeth on a digital or virtual teeth modeling set-up.

4. Once anchor points are determined on digital teeth, the anchors can be transferred to mouth teeth using an aligner transfer tray.

Example Force System

An example approach for forces to be delivered by a removable plastic aligner is described. The approach starts with light forces applied to enable engaging the anchors to a first level of force, and to initiate alignment of teeth for progressing gradually (as treatment progresses, then the next series of aligners), then to an aligner that is rigid enough to applying correcting torque to the teeth. Retraction and space closure can be done simultaneously or in stages.

Forces are generated by gradually increasing the stiffness of aligners (from soft initial aligners to rigid aligners as treatment progresses). This concept is only possible by use of different materials and direct 3D-printing, as conventional plastic-working processes will not be able to make an aligner with different dimensions within the same aligner, or different pre-defined thicknesses within the same aligner; or soft/hard materials at variable thicknesses at pre-defined locations within the same aligner.

Properties of the 3D-printed plastic aligner materials need to be consistent with the following metal arch wire parameters to produce force levels of around 26 gm/cm$^2$ of root surface:

0.014 nitinol (0.014 inch diameter) or 0.018 nitinol (0.018 inch diameter) or 18×25 nitinol (rectangular) or 18×25 steel (rectangular).

These values can be achieved by addressing the modulus of elasticity of the plastic aligner material, selecting the correct force deflection curve of plastic aligner materials to match metal arch wires, controlling the thickness of the aligner, the cross-section of the aligner, and the engagement of the aligner in the anchors.

Due to 3D-printing processes, aligners are designed with smooth edges so aligner does not irritate the patient's gingiva and/or tongue, so soft tissues do not become inflamed or blend. The process also allows no sharp flange at the base of aligner near the gingival margin particularly on the lingual side, as no trimming operation is required, but which is the part of the conventional aligner manufacturing process (i.e., thermoforming of plastic film, followed by trimming, cutting, deburring, and a smoothing operation, etc.)

Some of the example divot anchor designs described herein can also be used in conventional manufacturing of aligners, i.e.; thermoforming a plastic sheet/film on 3D-printed dental model or conventional dental model, where a simple design of a divot anchor is sufficient, or other reasons decided by the dentist or orthodontist.

The example designs, compositions, and geometries of the example 3D-printed aligners are an important part of example orthodontia systems, particularly the anchoring design of the aligners, to move teeth at pre-designed positions and apply force at predefined locations on a tooth. So the design of example aligners based on anchor design is significant since the aligner has to fit on the divot anchor and the two components have to work in conjunction with each other, as well as the aligners have to be manufacturable by 3D-printing processes.

Other example design innovations, materials, and processes are described below.

Specific additive manufacturing processes, or 3D-printing technologies, may be specifically required for particular aligner designs. Likewise, specific material formulations and combinations may be called for. The direct 3D-printing of aligners resolves several issues facing current conventional manufacturing methods. Example processes can direct 3D-print an aligner with thin or thick parts, an aligner having variable thicknesses at desired locations, hard or hard/soft aligners, aligner with different properties at different locations by design, or by using different materials within an aligner in a single step using 3D-printing processes such as FDM process, SLS process, direct pellets fused deposition process, DLP process, SLA, multi-jet photo cured polymer processes, HP Multi Jet Fusion Technology, the CLIP process, etc.

The aligner which fits on above concept designs can be made of single material with variable thicknesses at desired location to achieve desired tooth movement (i.e., differentially increase the thickness to change the amount of force with same material). Or, an example process may exert force regionally with changing thickness, incorporating a design concept or by changing material within the aligner.

An example 3D-printed aligner may exert a more effective force with better control of manufacturing, and may have controlled thickness of the aligner in desired areas to exert forces needed to perform tooth movement in the desired direction based on size, root length, and surrounding bond support. This can reduce number of aligners needed for orthodontic treatment of the teeth.

Aligner can also be made of multi-materials with or without variable thicknesses at desired locations. Multi-materials can help to change the position of the vertical plane. One of the inventions is to alter the shape and structure of plastics to exert force regionally, by torqueing or pushing the teeth up.

The invention also includes use of multi-materials in the aligner layer-by-layer through thickness in vertical position or horizontal position during same cycle of manufacturing.

One example aligner design uses different modulus of elasticity materials for teeth at the front (front teeth) and back part (back teeth) of the patient's arch. Another aligner covers the teeth at different levels (height). In an implementation, hard and soft aligners are 3D-printed separately, bonded together, or hard and soft are printed in the same 3D-printing step on top of each other.

In an example process, the properties of an aligner (as a whole or at desired localized area) are modified after manufacture by exposing the aligner or its parts to different energy sources such as electron beam, microwave, UV light, LED curing light, etc.

An example aligner can be clear, white, or tooth colored, for example. White or tooth-colored aligners may allow the aligner to fill pontic spaces (missing teeth) by directly 3D-printing dummy teeth. The tooth-colored aligners can be made by adding pigments or color in the base plastics, or by painting or coating the aligner after it is manufactured by a 3D-printing process. One can also incorporate decorative or identification features. A polymeric medical grade coating can be applied after the aligner has been manufactured by some of the additive processes where it is desired to reduce surface porosity and improve surface smoothness.

The invention shows how to cover the teeth at different levels, or some teeth, or leave an area not to be covered. The treatment can start with a series of aligners with hard followed by soft and so on. Three-dimensional control of misaligned teeth may start with a soft aligner.

One can have day and night appliances separately, where night appliance can have different thickness. It is also possible to adhesively join or ultrasonically weld 3D-printed hard and soft appliances to get a single aligner having hard/soft surface parts.

The patient should typically wear the aligner all the time except eating food or drinking hot liquid. Patient compliance is a major issue. One of the innovations is to incorporate die or pigment into plastic or coating of one of the molar internal teeth with this coating containing this dye or pigment. This die or pigment works as sensor, the color slowly goes away as time passes in the presence of mouth fluids (As color fades away, it indirectly tells patient or dentist the time duration aligner was in mouth). This may increase the compliance of wearing the aligner. If the patient is wearing the aligner as planned, and if dye fades away, it means that particular aligner has done its job, patient does not have to keep on wearing the aligner, it tells patient to switch to next aligner, which can significantly reduce treatment time for patient. Also, this dye concept can help dentist to determine if teeth movement is not occurring as planned. A micro-chip with small embedded sensors (such as temperature sensor) may also be included in an aligner to detect tooth movement over time and the compliance level of the patient.

An example aligner may incorporate a microchip on the aligner (inside at interface between aligner and tooth) with a force sensor that measures the forces that act on the tooth interface. The aim is to give feedback how well aligner is functioning, reduces the duration of therapy, related expenses and discomfort of individual as well as compliance information. A micro-sensor can be placed on a divot attachment to measure load/force values to see performance of the aligner as predicted by software and provide information remotely to orthodontist as well as patient.

An example aligner may have 3D-printed school logo or other design, or a very thin low modulus film with different designs which can be attached onto it for better appearance.

The aligner may function as sleep apnea or anti-snoring device by connecting the upper and lower aligners together and moving the lower jaw forward or making upper aligner with front hollow housing and side half round hollow tubes or center tube from the front housing which can bring more air while breathing, opening the air passage, reducing the snoring.

The aligner can also be used as mouth guard and night guards to prevent grinding of teeth.

The innovative material(s) and design of aligner is elastic in nature which means it exerts comfortable force when patient wears it and upon exert of force the aligner may extend/stretch but returns to original position to exert a gentle constant force to help programmed teeth movement. The material should not relax and lose energy in initial days of aligner wear. The thermoplastic material that exhibits substantial linear elastics behavior with a high yield point is more desirable. Creep, fatigue and dimensional stability properties of polymers are also important.

Proposed materials for Thermoplastic 3D printing process are polyurethane (TPU), polyamide, polyester or co-polyester such as PETG, polycarbonate, PMMA, polypropylene, polyether sulfone (PES) etc. For thermoset 3D-printing processes such as SLA, DLP etc, photopolymer acrylic resins can be used to achieve the desired material properties.

One of the materials that can be 3D-printed is self-reinforcing plastics. The benefit of this material that it does not have fibers, but the polymer itself helps in controlling the aligner's properties. This material has a high elastic modulus, no deformation after desired strain, toughness, and high strain at break.

The plastic powder particle size for SLS process is very important to have dense fusion. The particle size is in the range of 20-100 microns. Less than 50 microns is more preferable. It is important that the aligner not crack during handling. High material elasticity with better material fusion and density are some of the innovations for 3D-printing material and process. One of the inventions is to combine different family plastics powders (such as nylon with TPU) having very close particle size distribution to obtain desired modulus of elasticity and more isotropic properties (same properties in X, Y and Z direction, which is difficult to achieve in case of SLS process). To achieve the above-mentioned design concepts and 3D-printing processes, the innovative developed materials may have the following properties:

The materials may have biocompatibility as per DIN EN ISO 10993 and US Type VI standards.
Hardness—Shore D scale of 40-90 (DIN 53505)
Elastics Modulus—1000-1800 Mpa (ASTM 638-2010)
Tensile strength at yield—40-70 Mpa (ASTM 638-2010)
Off set yield stress—greater than 25 Mpa (ASTM 638-2010)
% elongation at break in the range of 80-200% (ASTM 638-2010)
Flexural strength—50-70 MPa (ISO 178)
Flexural Modulus—1200-1500 MPa (ISO 178)
Tear strength in range of 45 MPa to 60 Mpa
Energy to break—16-20 Joules
No deformation in the range of 0.5% strain over an 8-24 hour period
Stress relaxation rate (N/s) in the range of 0.010-0.020
Impact properties: notch impact at 23° C.-16 kJ/m$^2$ (DIN 53453)
Properties as measured by nanoindentation tester (ASTM E2546):
Elastic (Young) modulus in the range of 600-2000 MPa
Hardness in the range of 40-160 Mpa, preferably the range is 40-80 Mpa
Creep (nm) in the range of 120-400 nm.

The orthodontic system may use a total digital or total virtual concept. The patient or orthodontist can take the digital impression using nano intra-oral scanner, smart phone having attached extended camera or WiFi camera transferring the digital data to a smart phone or other device to create a .STL file of teeth. The camera may be independent of smart phone or other digital device (attached to phone by wire or wireless). Orthodontist or other dental professional can design series of aligners based on final desired teeth movement and can 3D print these aligners at his office during patient's first visit or can send .stl file to out-side service labs who 3D prints the aligners for orthodontist or dental professional. As teeth movement occurs, take digital impression again, make new aligners as described above or using available software, make series of aligners for certain amount of teeth movement before calling the patient back in office. This is less iterative, fast and low cost solution.

Above described total solution of innovations in design, innovation in materials and incremental process improvement open up lot of design freedom and options in treating the patient in short amount of time and certain non-feasible cases which are not possible now. It can be cost effective, more precise, and more comfortable to patient.

Example Processes
For FDM Process:

A new concept allows printing of different materials not only in X and Y direction but also in Z direction. Also using hybrid process, using robotic extruder heads it is possible to print multi-material during or after part is made.

The example system also includes use of single filament having two different molecular weight materials to get hard/soft aligner in a single step process. During 3D-printing, low molecular weight material which is soft comes on the surface. Or one can use two layer filament where outer layer is made of soft material. Inner layer is hard material of same polymer or different but compatible polymer.

For SLS Process:

To get a hard and a soft material in same part, mainly to get soft or hard material on the surface of the part, example material formulations may be used. The material consists of low and high molecular weight materials. After the part is made by laser sintering, the part can be exposed to high temperature, just below the melting point of low molecular weight material, this causes the low molecular or soft material to come on the surface, building very thin layer of soft material on surface.

One example technique increases the modulus of the aligner as a whole or localized area by crosslinking of part after it is made or during the part fabrication.

Another example process adds a specialty coating, which provides a smooth surface.

An example technique combines different families of plastics powders (such as Nylon with TPU) having very close particle size distribution to obtain desired modulus of elasticity and more isotropic properties (same properties in X, Y and Z direction, which is difficult to achieve in case of current SLS process)

For SLA Process:

First the part can be made from one material, mainly photopolymer. Then, this part is inserted in the liquid of different material where other material is cured on the surface of first part. The invention is to get part with different softness and also additional features with second material.

DLP, or digital light processing, is a similar process to stereolithography in that it is a 3D printing process that works with photopolymers. The major difference is the light source. DLP uses a more conventional light source, such as an arc lamp, with a liquid crystal display panel or a deformable mirror device (DMD), which is applied to the entire surface of the vat of photopolymer resin in a single pass, generally making it faster than SL.

For FDM process, to increase properties in Z direction, the crystallization kinetics of the material are changed to get better heat retention and hence higher inter-layer bonding between layers in Z layers.

To improve fusion properties and shrinkage properties of SLS materials, fillers like silica powder, glass microspheres etc., are added. To improve impact properties and reduce modulus of elasticity still applying constant force without aligner deformation, elastomers like TPE in rigid plastics like nylon can be added.

In another system, dual modulus material is used in the same part for SLA process, to get low modulus in certain area of the part, photopolymer is cured with laser beam with low frequency while rest of the part is cured with laser beam with high frequency to get an aligner with dual modulus with in the same part.

Figure 18:
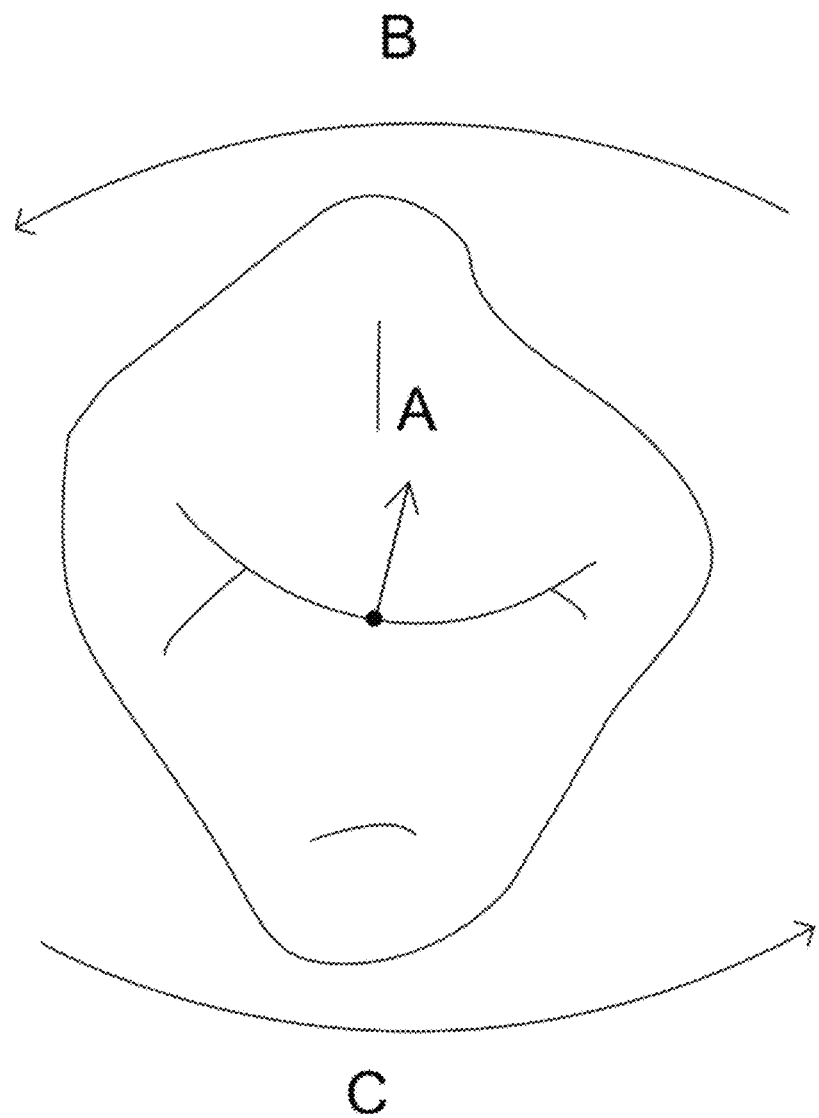
FIG. 18 is a diagram showing an example force distribution needed for effective rotation movement.

The various hardware described above, such as the example anchors and 3D-printed aligners, can be used to effect rotation for correcting tooth misalignment. As shown in FIG. 18, correction of rotation (of a tooth) in orthodontics is achieved by creating a couple around an axis of rotation (two equal and opposite forces B and C of the same magnitude acting around the same rotational axis A).

Figure 19:
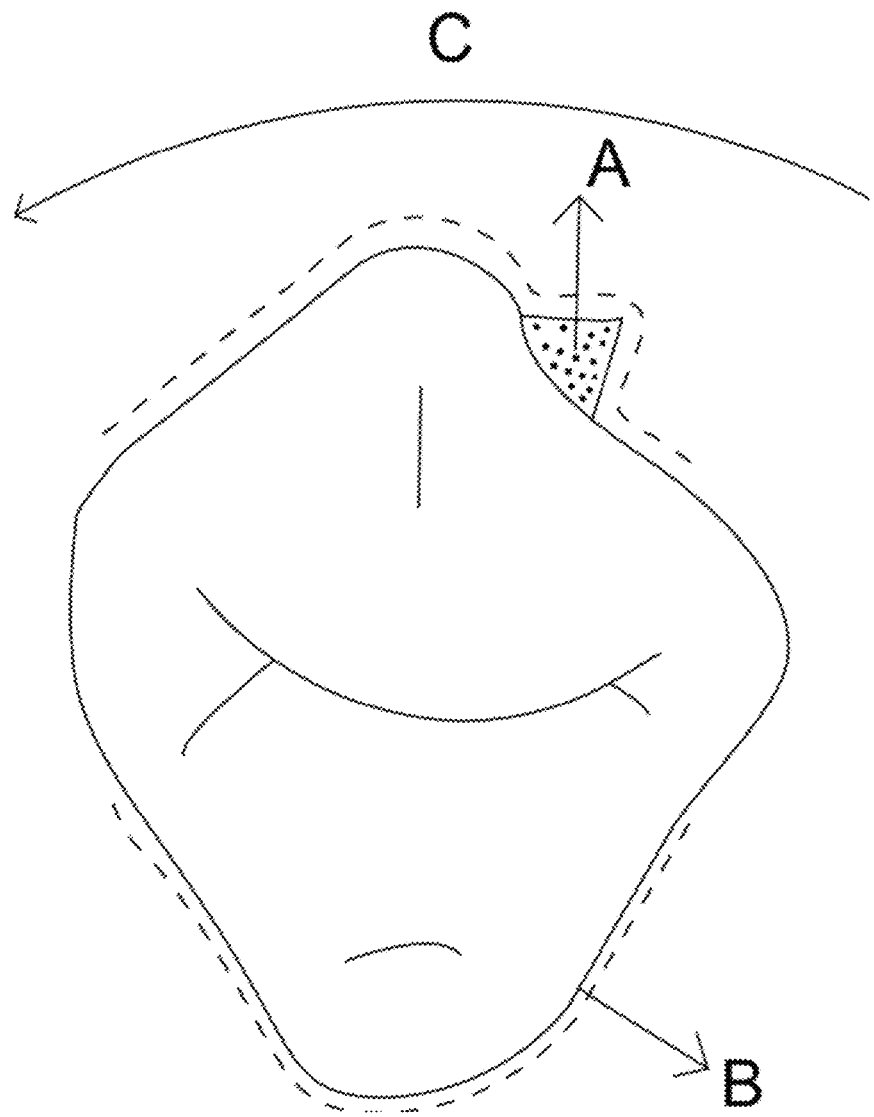
FIG. 19 is a diagram of prior art showing conventional INVISALIGN mechanics, with the corresponding aligner made by thermoforming.

Currently with a conventional INVISALIGN aligner, correction of rotation is been achieved by a push rotation. As shown in FIG. 19, prior art, device A is an attachment on the tooth. The dotted line B shows an aligner and C is the force direction. Attachment A allows for force to be generated in a push direction C, but there is no force in an equal and opposite direction, as there is in FIG. 18.

Thus the INVISALIGN aligner and other aligner designs on the market are very inefficient, further adding to a problem that there is too much resistance on the contralateral side (opposite side), because the conventional aligner contacts with the tooth.

The following describes three example designs for improving rotation correction. First, in FIG. 20, A is a divot anchor, the dotted line B is an aligner, C is a space for reducing resistance, D is force in one direction, and E is a spacer to reduce resistance in the other direction. In an implementation, a preferred method of manufacturing an aligner uses 3D-printing as such printing has a high degree of design freedom and other benefits as described. But, the example aligners for use in conjunction with one or more divot anchors can also be made by other CAD/CAM methods or even a conventional thermoforming process, if the particular design and costs permit. A conventional aligner cannot have thick section to fit into depression of the divot anchor (i.e., variable wall thickness, thick and thin), a conventional aligner only configures to the wall or outside plane of the depression of the divot anchor due to limitations of the thermoforming process. Example design and dimensions of a divot anchor are shown in FIGS. 1-4.

Using the described hardware, an example technique applies a pull force on the one side (for example on buccal side—the surface of a posterior tooth facing the cheeks) with a defined point of application using the divot anchor on the tooth. Placement of the divot anchor is easier that conventional placement of a rotation device, as shown in FIG. 20.

Figure 20:
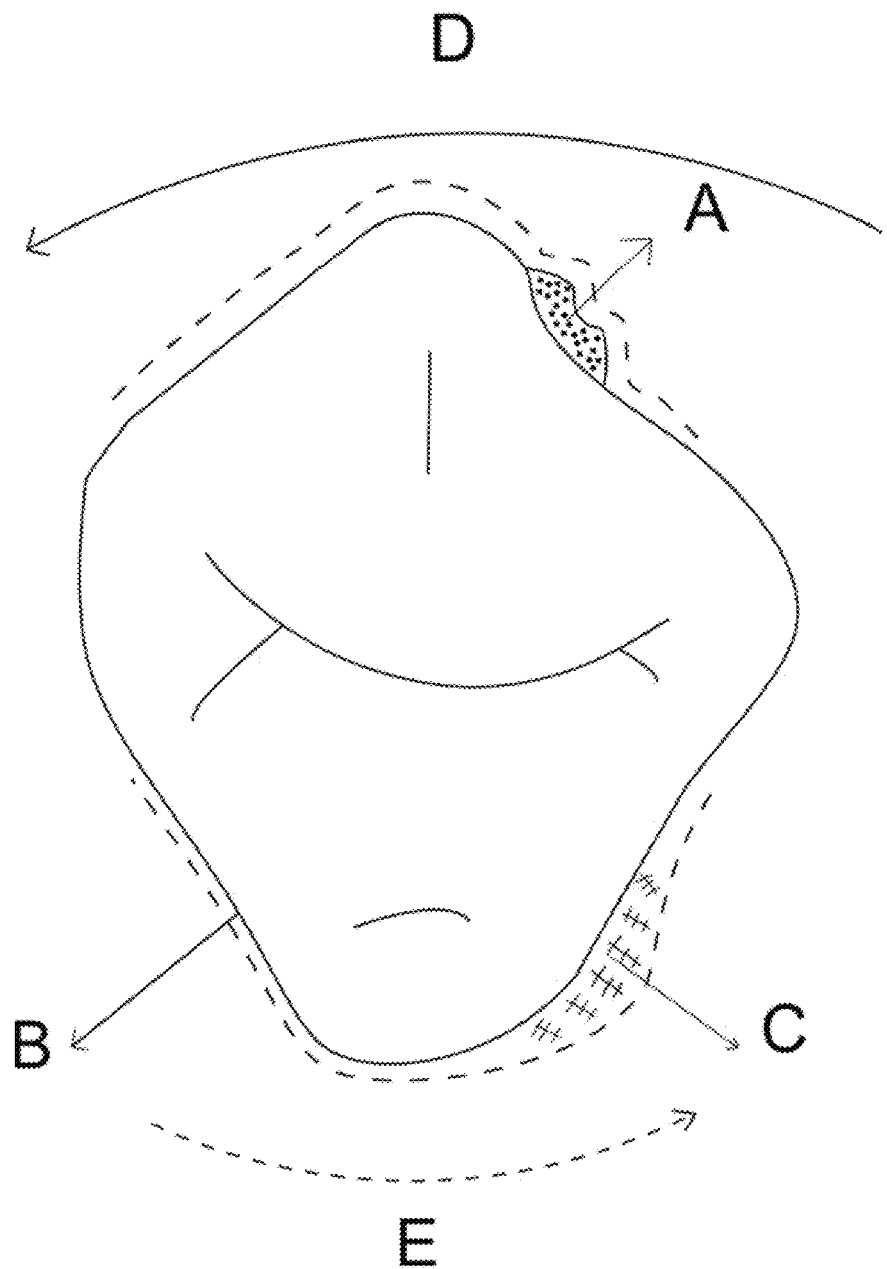
FIG. 20 is a diagram showing an example design to reduce reciprocal resistance in order to induce rotation caused by primary force.

As also shown in FIG. 20, the technique then includes creating a space for tooth to move on the lingual side (the surface of a tooth facing the tongue) ipsilateral position to reduce interference.

Figure 21:
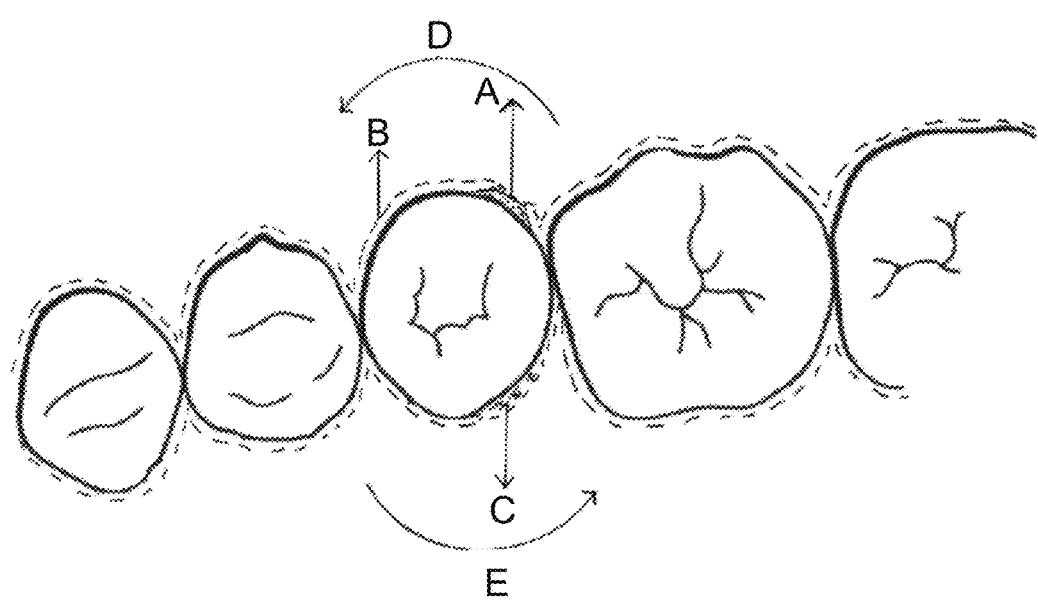
FIG. 21 is a diagram showing an example occlusal view of the concept of FIG. 20.

FIG. 21 shows a top view of teeth using the example set-up of FIG. 20.

Figure 22:
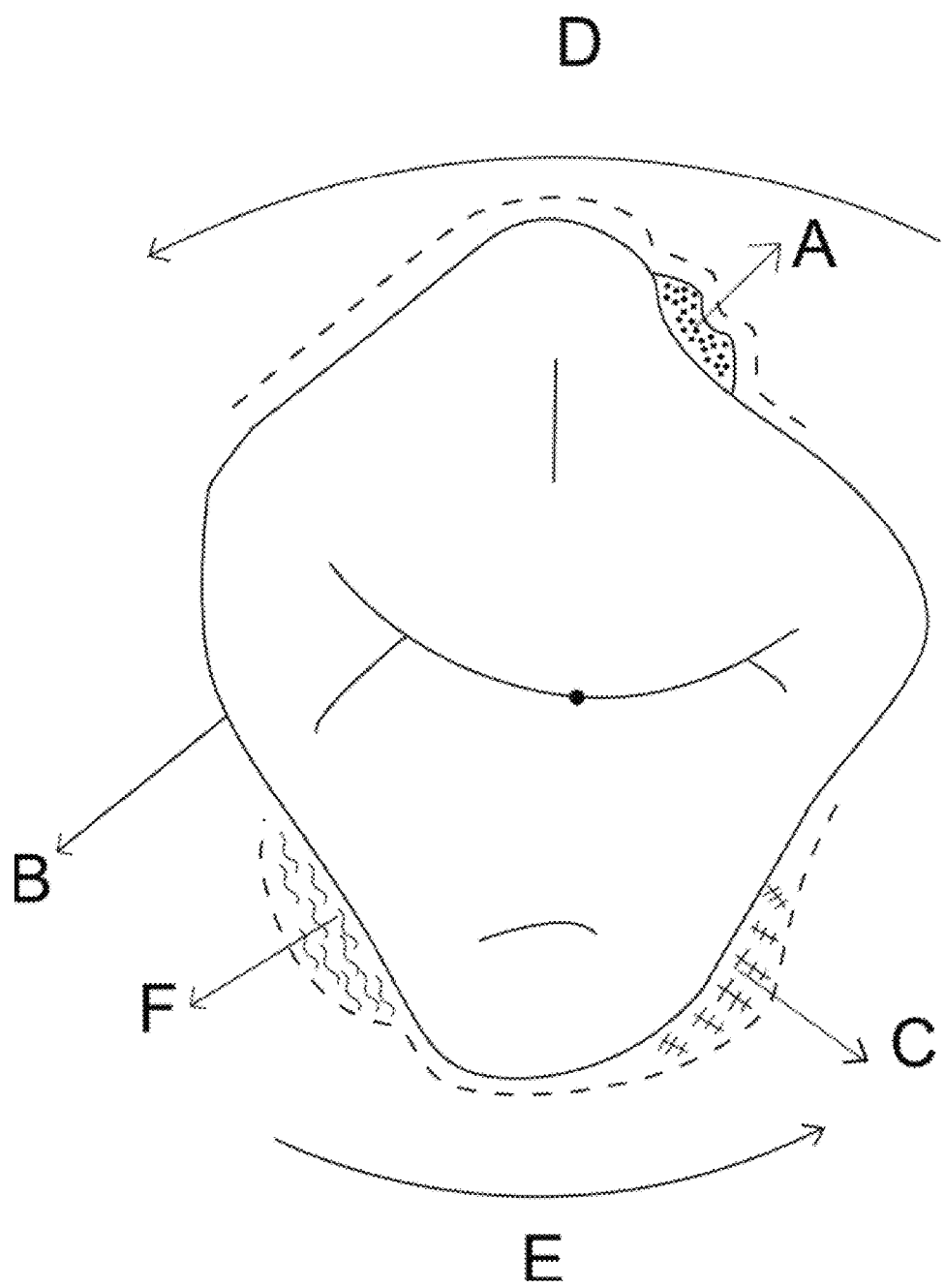
FIG. 22 is a diagram showing an example technique to produce equal and opposite force on the lingual aspect generated by soft aligner material diagonally opposite to an example divot attachment and spacer for allowing a tooth to move.
Figure 23:
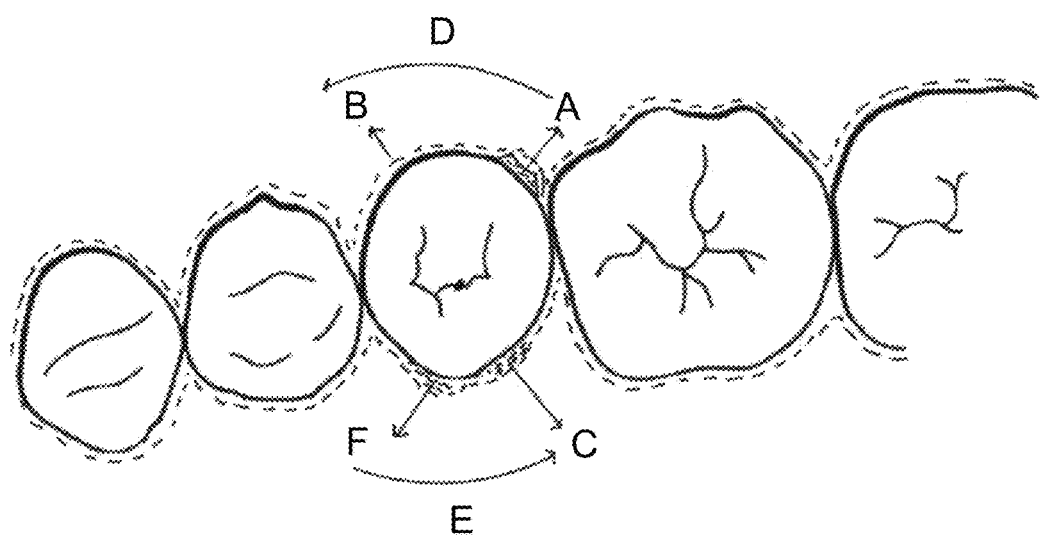
FIG. 23 is a diagram showing an example occlusal view of the concept of FIG. 22.

In a second example method for correcting rotation, the rotation control is achieved by creating a couple. As shown in FIG. 22, a space C reduces resistance to movement and F is soft reline material exerting an equal and opposite force. Force D and force E are equal and opposite forces created by the soft reline. So, this example rotation control using the couple concept is achieved by adding soft material F on the contralateral side diagonally opposing the buccal forces to act as another push component. FIG. 23 shows a similar top view.

Figure 24:
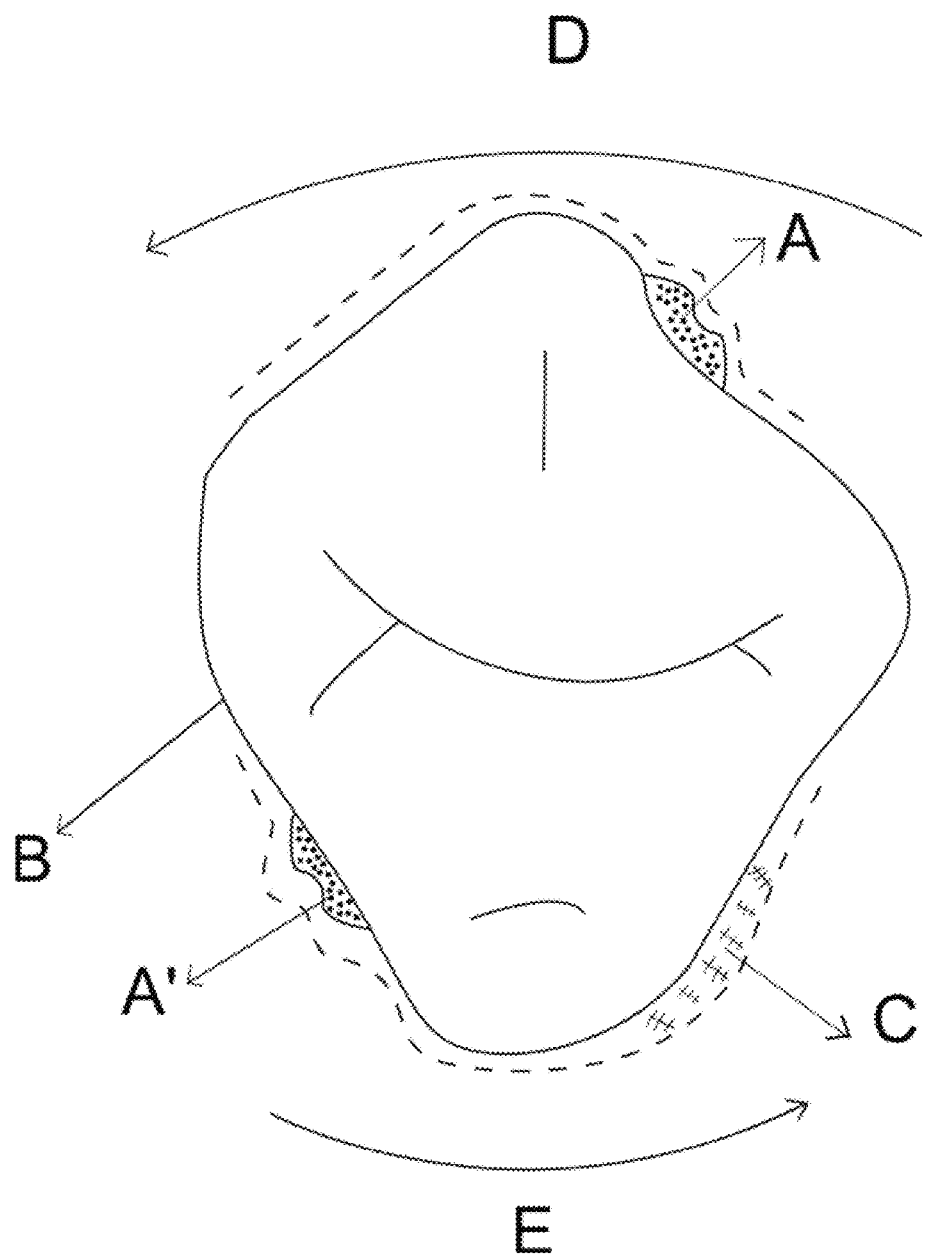
FIG. 24 is a diagram showing example force created by an attachment "A" and equal and opposite force created by second attachment "A" diagonally placed and a spacer to allow the tooth to move.
Figure 25:
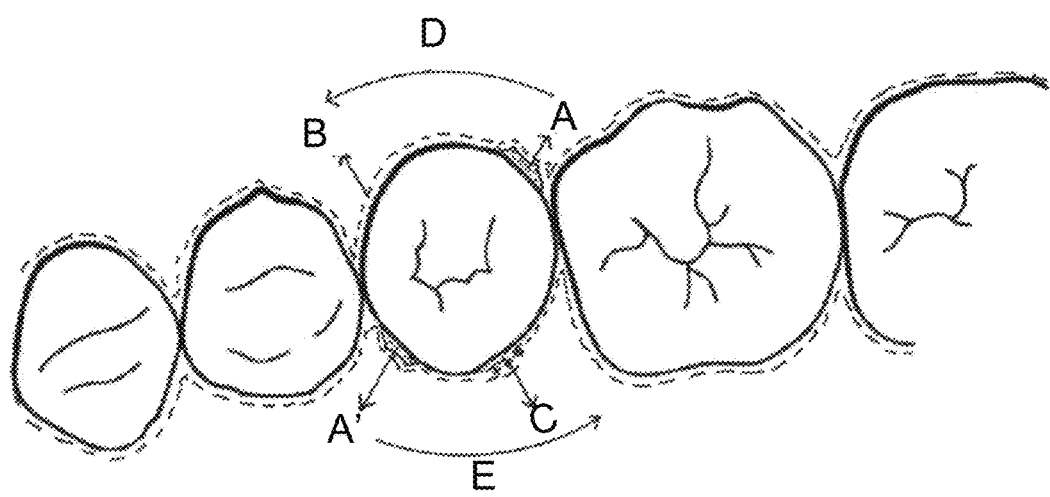
FIG. 25 is a diagram showing an example occlusal view of the concept of FIG. 24.

Another way to achieve this aim is to add a divot anchor on the lingual side also (the surface of a tooth facing the tongue). This scenario is shown in FIG. 24, where A is the divot anchor and A' is a second divot anchor diagonally opposite on the opposing side of the tooth. FIG. 25 shows a top view of this concept, showing multiple adjacent teeth.

Figure 26:
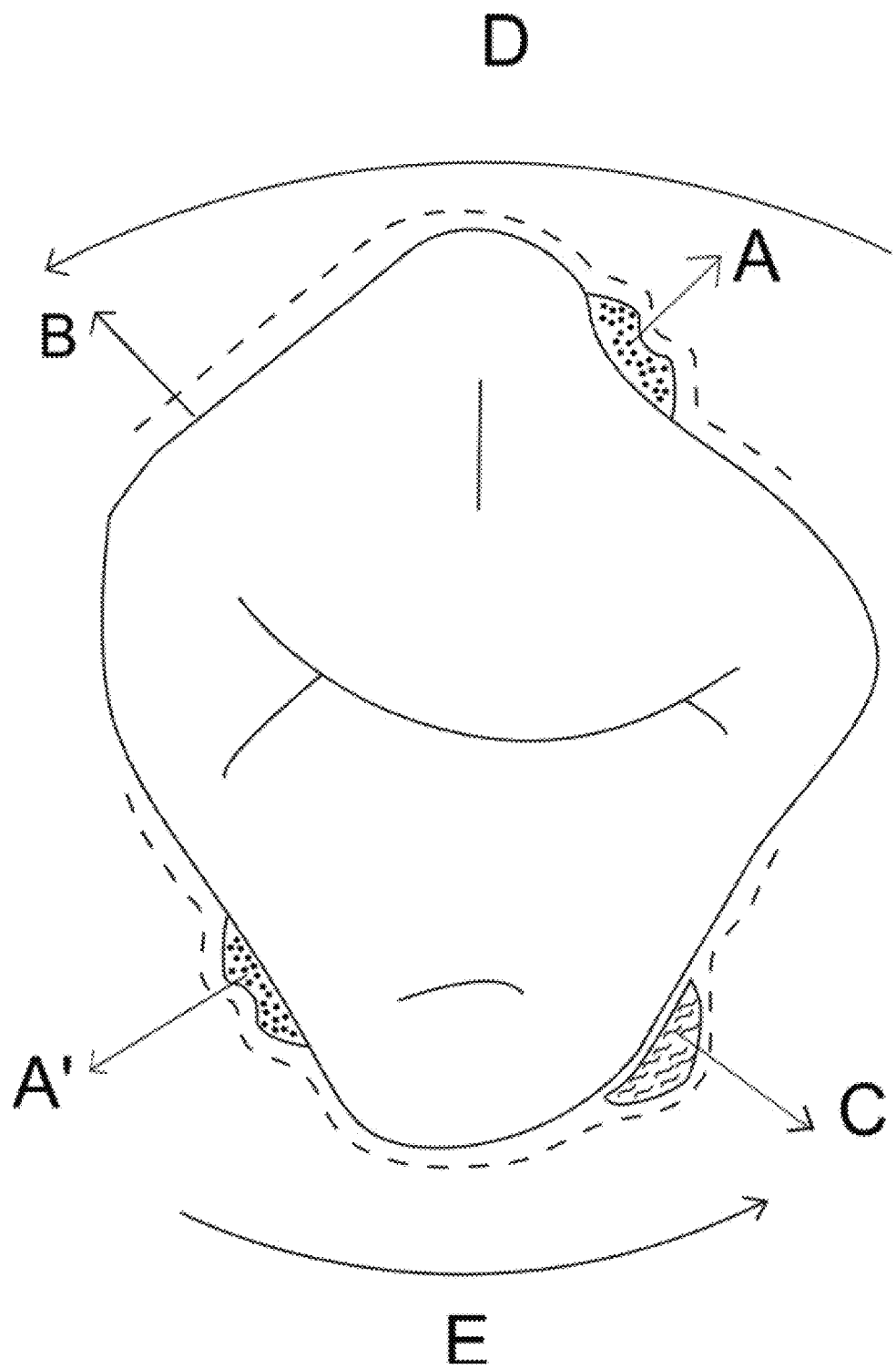
FIG. 26 is a diagram showing an example rotational movement created by a force generated at example divot anchor "A" and reciprocal movement created by second anchor "A" and movement enhanced by a pull force via suction cup attachment "C."
Figure 27:
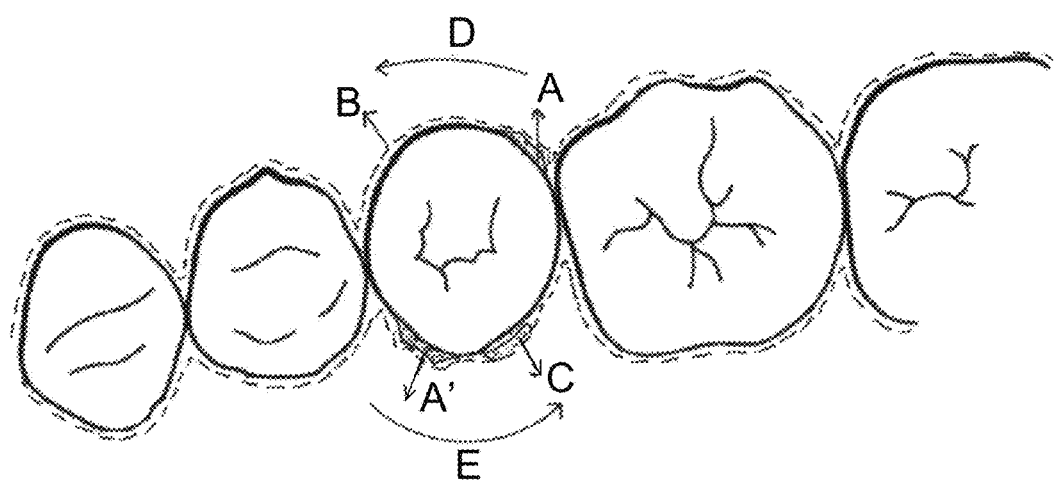
FIG. 27 is a diagram showing an example occlusal view of the concept of FIG. 26.

The third example method for correcting rotation includes adding a soft material on the lingual surface on the ipsilateral side, the soft material being designed to act as a suction cup. The concept is shown in FIG. 26. Divot anchor A and divot anchor A' are diagonally opposite on the tooth. B represents an example aligner and C is a spacer to reduce resistance. C can be a honeycomb suction cup made of soft material or other design and material that can provide the suction. D is a rotational force and E is an equal and opposite force rotational force. There are various materials and design concepts for creating suction to the aligner. FIG. 27 shows a top view of this concept, showing multiple adjacent teeth.

Figure 28:
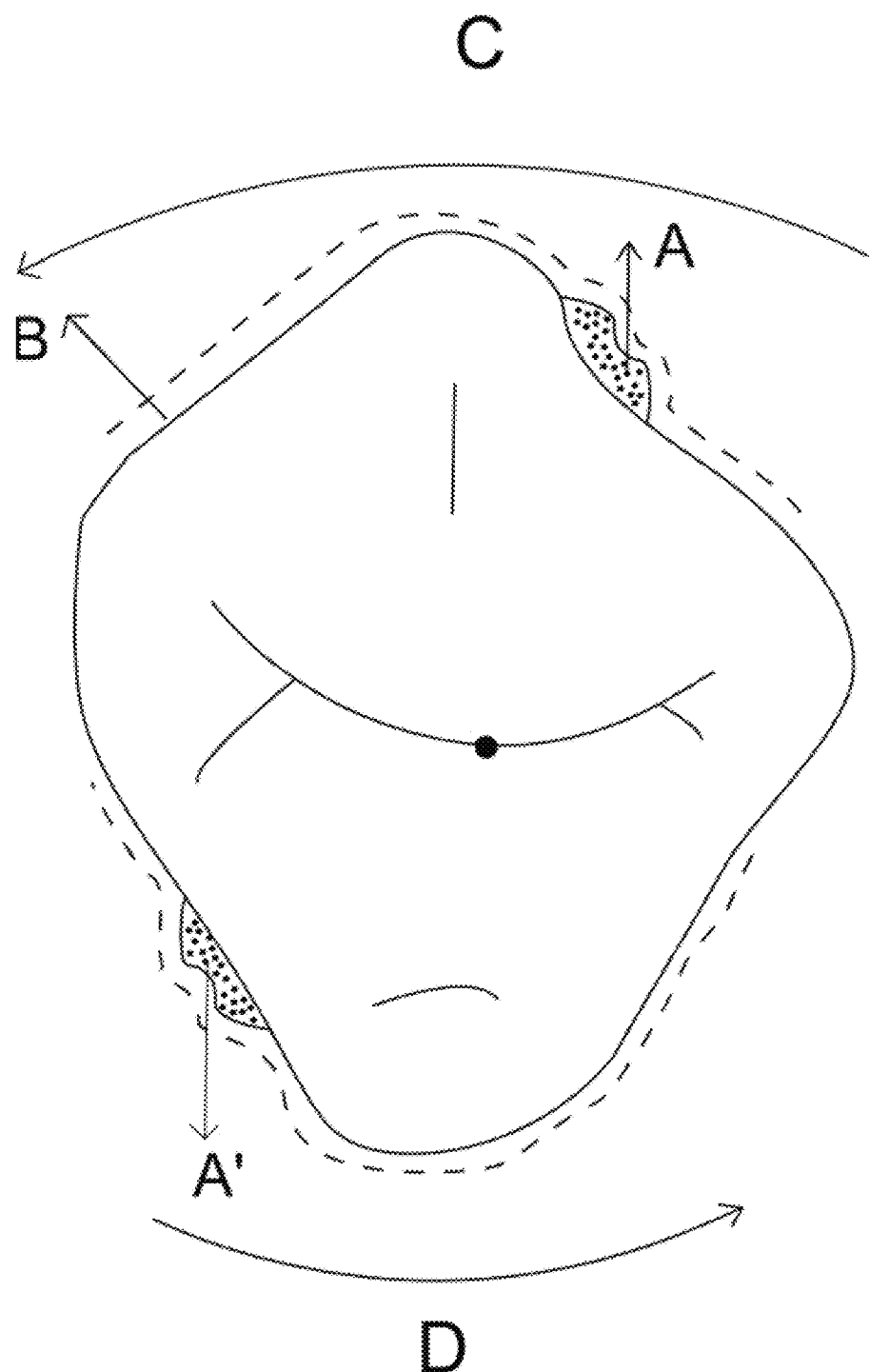
FIG. 28 is a diagram showing an example force created by attachment "A" and equal and opposite force created by second attachment "A" diagonally placed.
Figure 29:
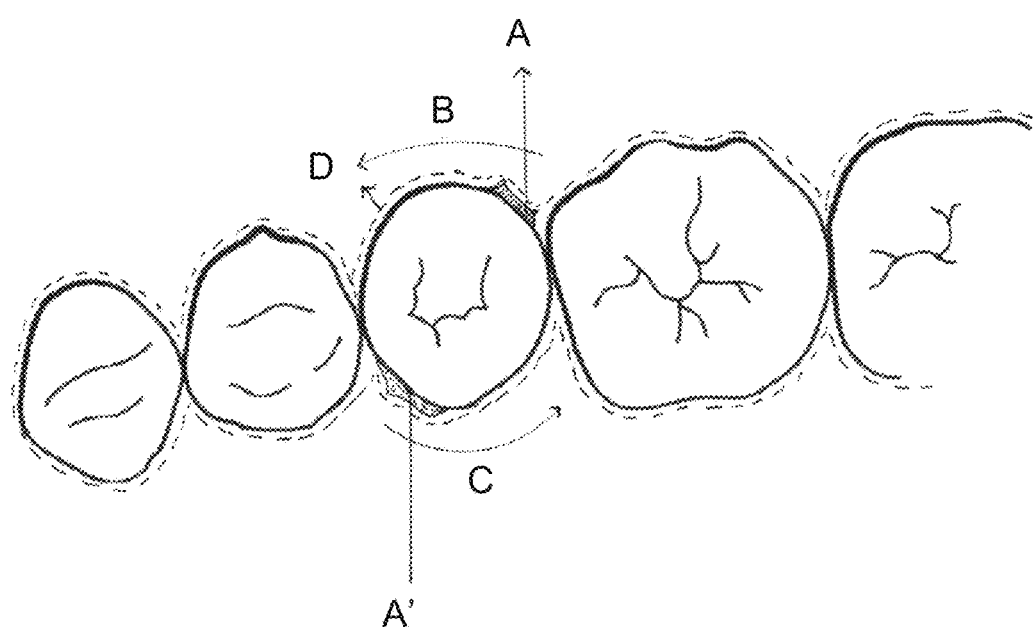
FIG. 29 is a diagram showing an example occlusal view of the concept of FIG. 28.

FIGS. 28-29 show the same concept as in FIG. 24, but with no space provided for reducing resistance.

Advantages of an example divot anchor include:
Smoother to tongue and cheek
Provides a more precise area for force application
Since the divot anchor is flatter than conventional, it can be placed in areas where there is less space
On anterior teeth, the divot anchor can be made into a rectangle (simulating a bracket slot of a conventional orthodontic bracket). Applying force to the soft material can be delivered by lining the aligner with soft material.

Torque Control of Anterior Teeth

Figure 30:
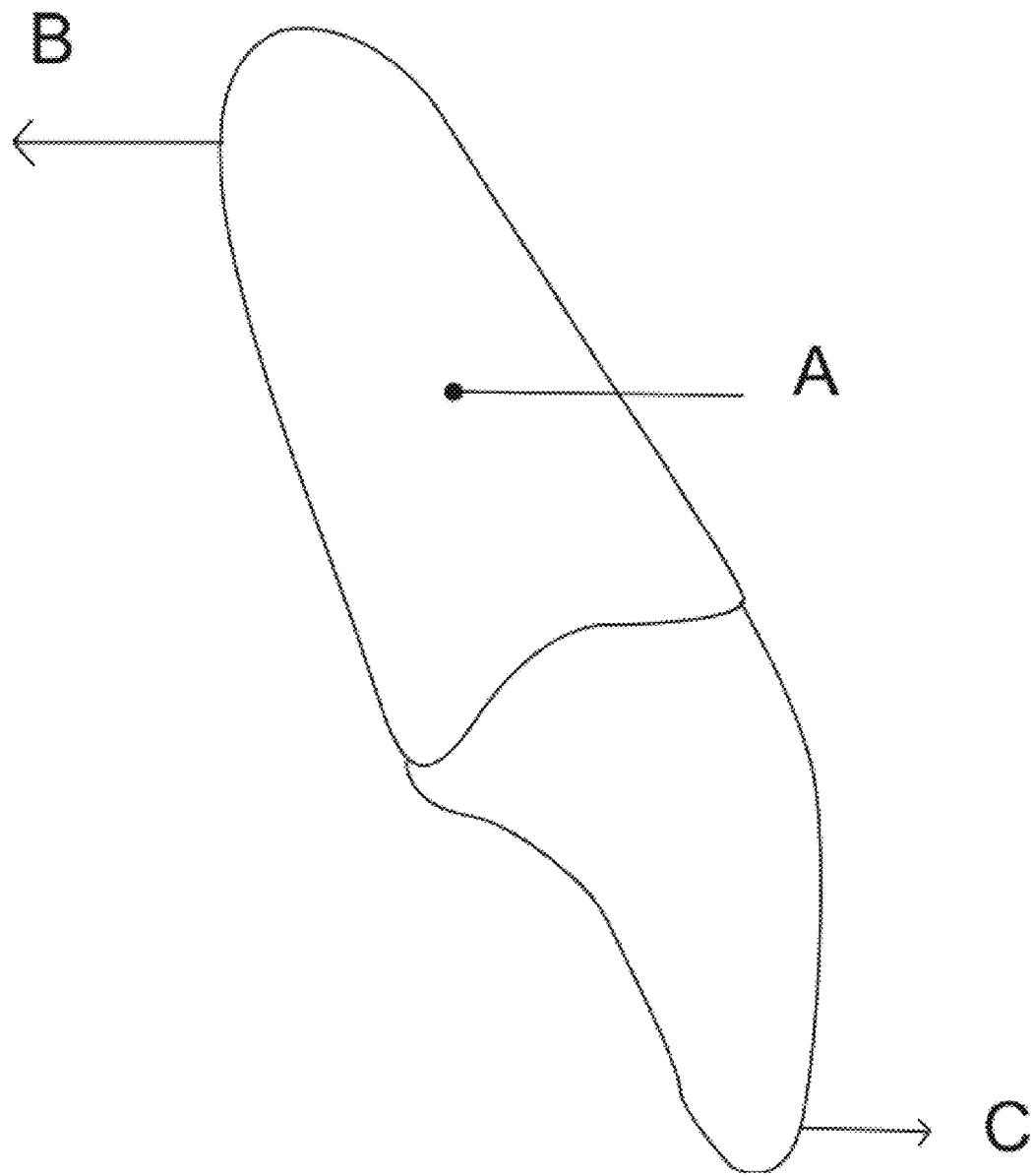
FIG. 30 is a diagram showing example forces required for torqueing roots of teeth.

As shown in FIG. 30, A is a center of resistance, B is a root moving palatal and C is reciprocal crown movement. This type of movement is needed for a tooth so that the root moves to the center of an alveolar process.

Currently with conventional braces, torque is created in teeth by applying force in a labial-lingual direction. Although the intention is to move the root either in buccal or lingual directions, the crown always needs to move in the opposite direction, although not as much in magnitude. To achieve this movement, there should be complete engagement of the wire (the source of force) into the bracket and the system should be rigid.

Figure 31:
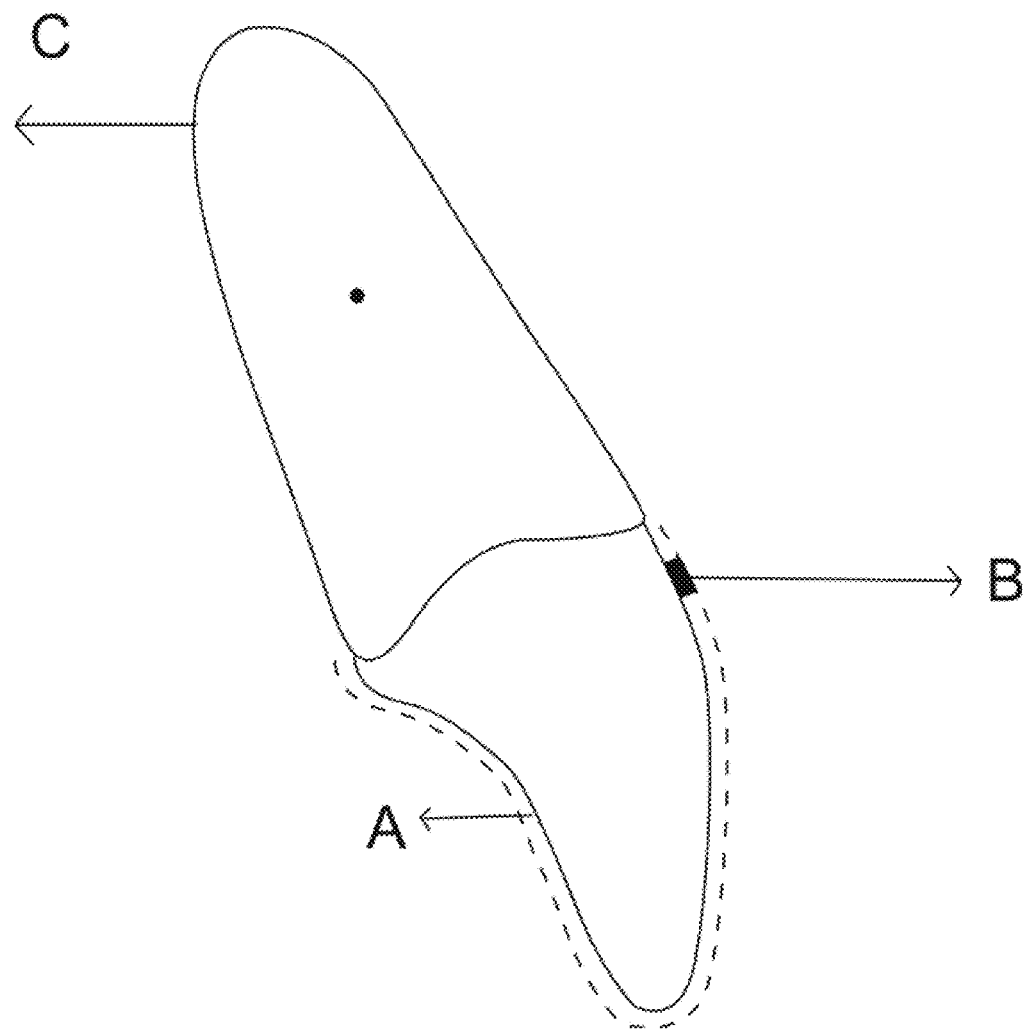
FIG. 31 is a diagram showing a prior art torqueing mechanism of an INVISALIGN thermoformed aligner.

The conventional design of the INVISALIGN aligner applies torque by creating contact of the aligner towards the gingival one-third of the tooth with power ridges. FIG. 31 (prior art) shows this approach, in which A is a conventional aligner, B is power ridge, and C is the intended force direction. There is no room for reciprocal crown movement.

Disadvantages of the conventional aligner are that the power ridges do not have a definite point of engagement, and therefore the conventional aligner does not fit on the tooth completely, which in turn reduces the efficacy of the conventional aligner system.

In an implementation, a proposed improvement creates a better engagement of the example aligner at the point of force application by making the aligner engage into the divot anchor on the buccal side towards the gingival margin, while creating spaces on the opposite side to reduce resistance.

Figure 32:
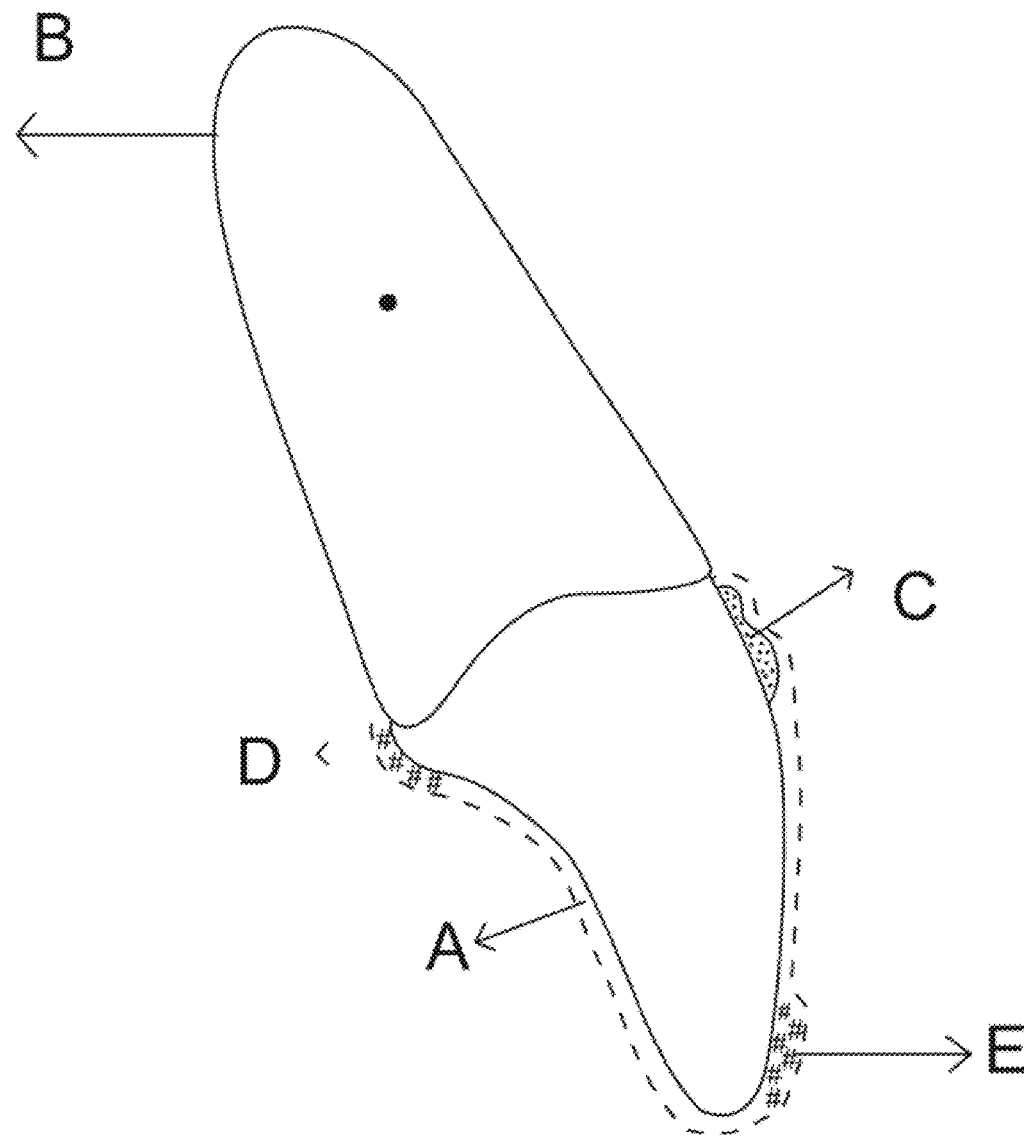
FIG. 32 is a diagram showing an example new design for torqueing anterior teeth.

This scenario is shown in FIG. 32, in which A is an example aligner, B is the intended direction of force, C is an example divot anchor for definitive engagement of the example aligner, D is a spacer to reduce resistance, and E is a soft material to allow controlled reciprocal movement of the crown. To enhance controlled movement of the crown, soft material may be added on the incisal one-third of the crown on the labial side.

Figure 33:
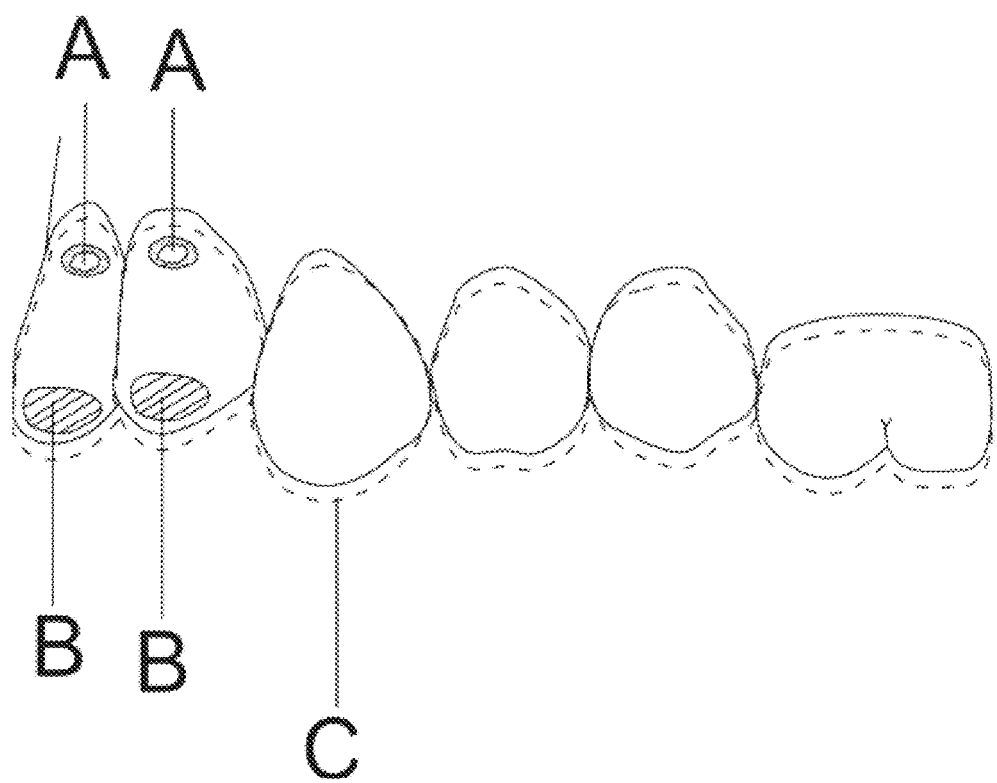
FIG. 33 is a diagram showing a buccal view of an example torqueing mechanism.

FIG. 33 is a buccal view of an example torqueing mechanism showing A as the example divot anchor and B as the soft reline to allow reciprocal crown movement.

Figure 34:
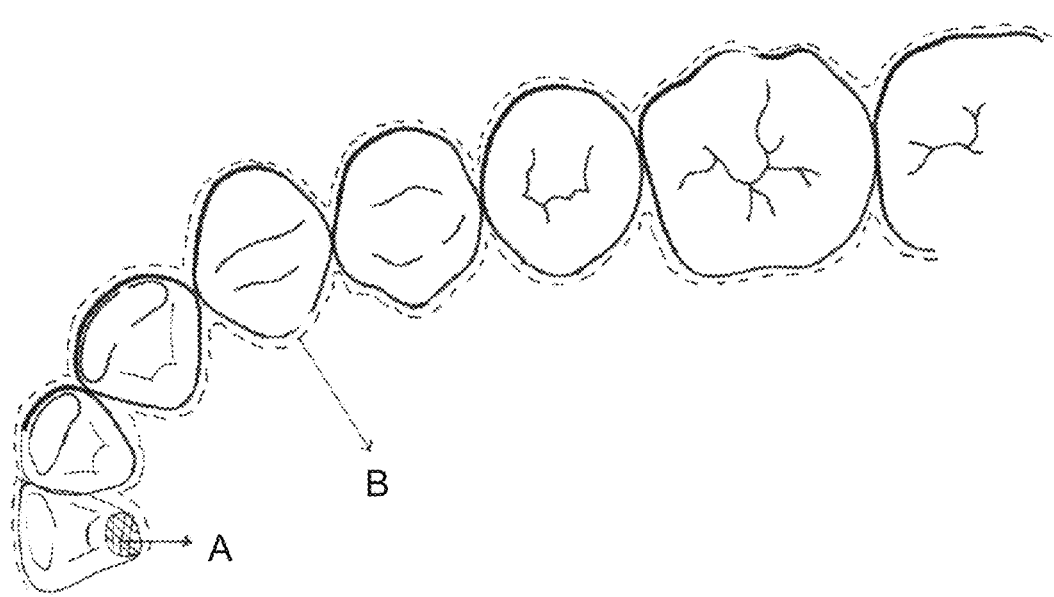
FIG. 34 is a diagram showing an occlusal view of an example torqueing mechanism.

FIG. 34 is an occlusal view of an example torqueing system showing the torqueing mechanism and space at the level of the cingilum of the center incisor. Spacer A reduces resistance for palatal movement of the cervical part of crown, and B is an aligner.

Figure 35:
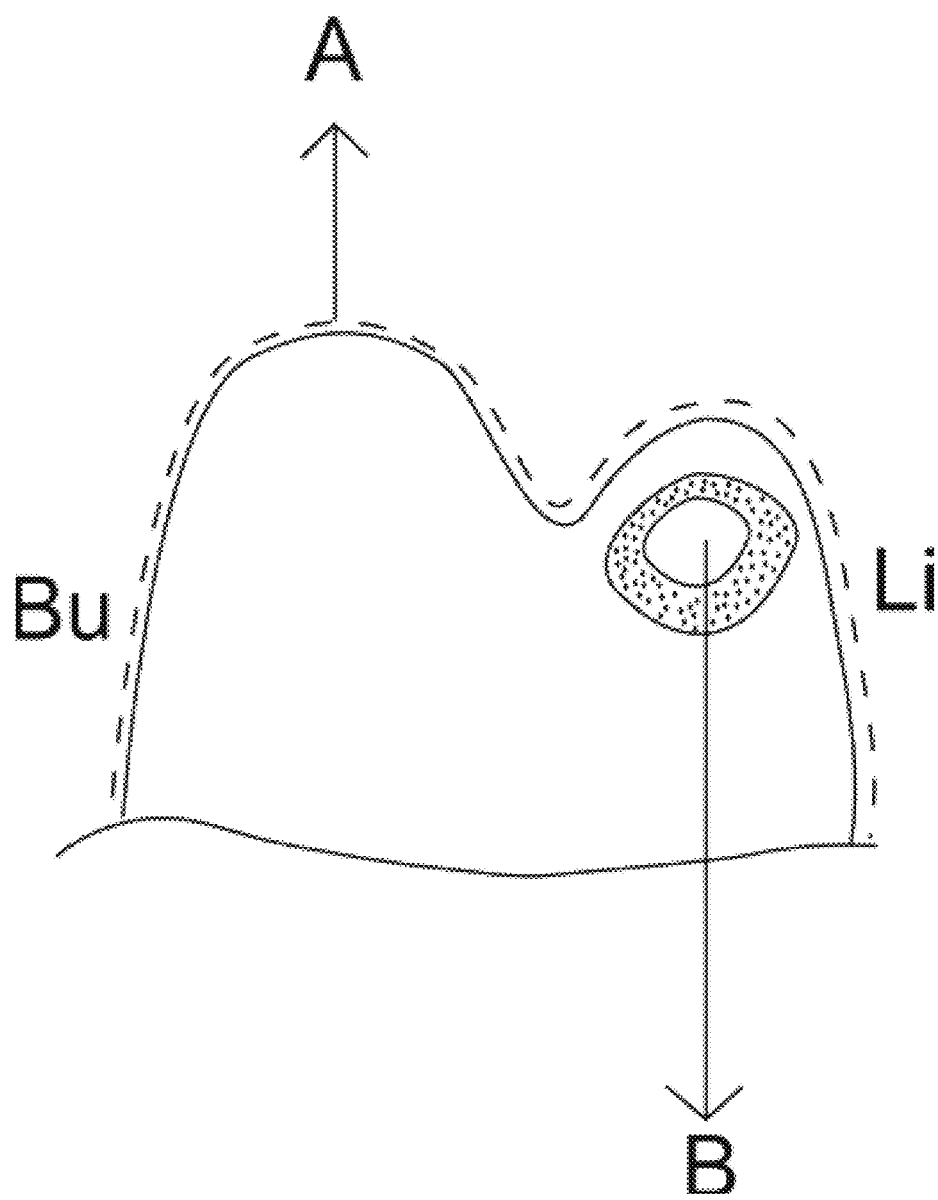
FIG. 35 is a diagram showing a mesial view of example rotation mechanics.

FIG. 35 shows a mesial view of rotation mechanics showing the example divot anchor and its approximate placement on the buccal side to cause mesiolingual rotation. Here, A is the example aligner, and B is the example divot anchor. Bu represents the buccal surface, while Li represents the lingual surface.

Figure 36:
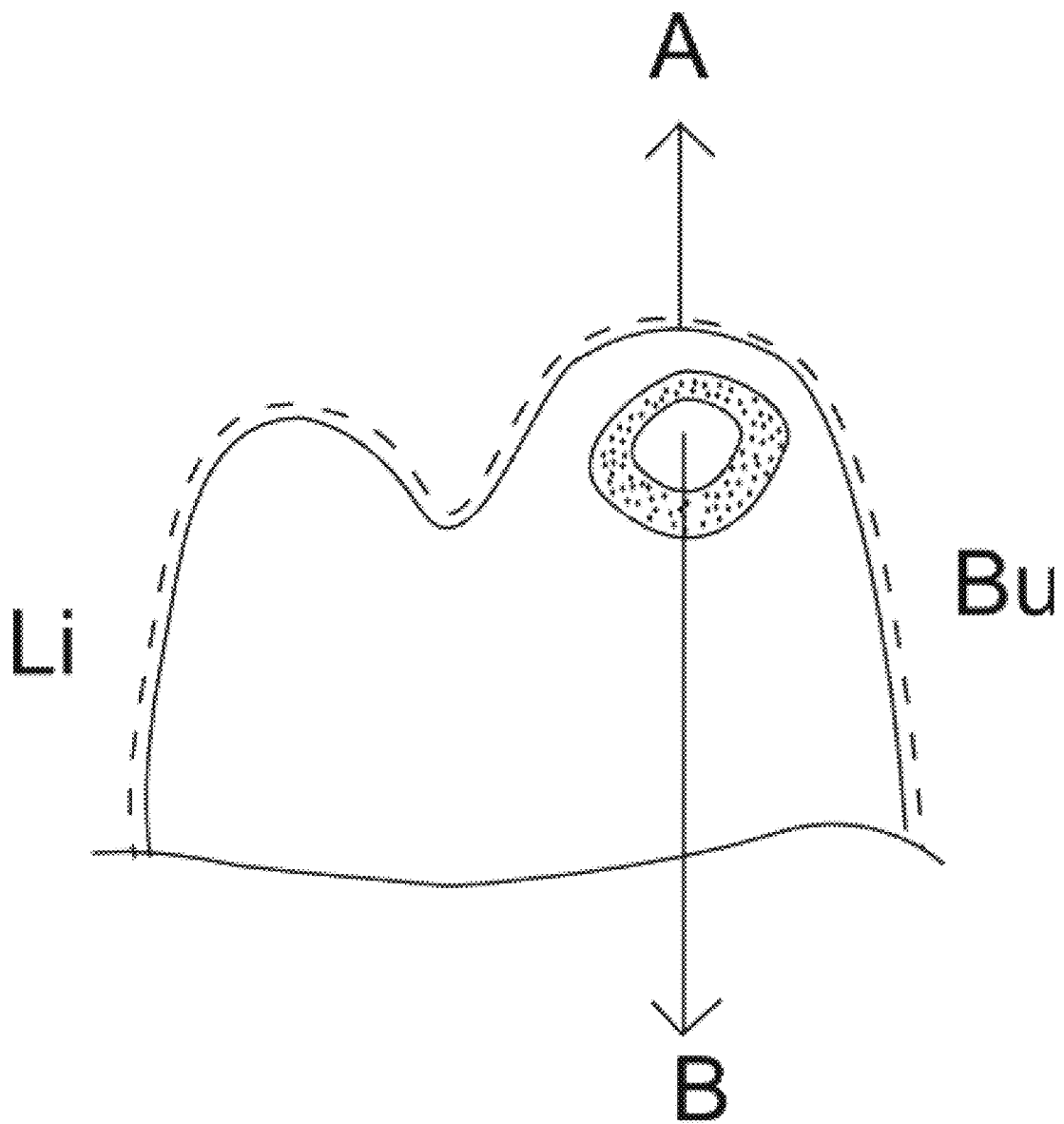
FIG. 36 is a diagram showing a distal view of example rotation mechanics.

FIG. 36 is a distal view of rotation mechanics showing approximate placement of a divot anchor attachment on the lingual side to cause mesiolingual rotation. Here, A is the example aligner, and B is the example divot anchor. Bu represents the buccal surface, while Li represents the lingual surface.

In an implementation, an orthodontic system includes an aligner for fitting over one or more teeth to apply a force to at least one tooth, and at least one 3D-printed part of the aligner for applying the force to the at least one tooth. The at least one 3D-printed part may comprise a 3D-printed material capable of an elastic strain recovery for applying the force to the at least one tooth. The at least one 3D-printed part applies a torque, a rotational force, a leverage, a push, a pull, or at least part of a full 3D control force to the at least one tooth.

A divot anchor can independently attach to a tooth, wherein a geometry or an extension of the 3D-printed part of the aligner is configured to form a removable attachment with a divot of the divot anchor to apply a torque, a rotational force, a leverage, a push, a pull, or at least part of a full 3D control force to the tooth through the divot anchor.

Multiple divot anchors may each independently attach to a tooth, and the aligner applies a different force vector to the tooth through each of the multiple divot anchors.

The divot anchor may further comprise a groove, a channel, a notch, a depression, a cavity, or a hole for securing a tab, a flange, a rib, a hook, an extension, a geometry, or a member of the aligner for applying a force to the tooth, wherein the force comprises one of a torque, a rotational force, a leverage, a push, a pull, or at least part of a full 3D control force.

At least one 3D-printed part of the aligner may be constructed in an additive manufacturing process.

The system may further comprise a torque control feature of the aligner, the torque control feature comprising a space disposed between the aligner and at least one tooth. A compressible material may be disposed in the space between the aligner and the at least one tooth. The aligner may comprise a plurality of materials each having a different modulus of elasticity. The aligner may comprise a first material with a first modulus of elasticity for front teeth and a second material with a second modulus of elasticity for back teeth.

At least part of the aligner may be constructed in an additive manufacturing processes selected from the group consisting of a FDM process, a SLS process, a direct pellets fused deposition process, a SLA process or a DLP process, a multi-jet photo cured polymer process, a multi jet fusion technology, and a CLIP process.

An additive may be used that fades over a time interval upon contact with mouth fluids.

A microchip and a sensor may be included in the aligner to detect a tooth movement over a time interval or to measure a compliance level of a patient.

The aligner may comprise multiple thicknesses of a 3D-printed material. A pigment or a coloring agent may be included in the aligner, formulated to match a color of teeth. A polymeric coating may be placed on the aligner to reduce a surface porosity and to increase a surface smoothness of the aligner.

At least one 3D-printed part of the aligner may be composed of a material having a hardness on a Shore D scale in a range of 40-90, an elasticity modulus in a range of 1000-1800 Mpa, a tensile strength at yield in a range of 40-70 Mpa (ASTM 638-2010), a percentage elongation at break in a range of 80-200%, a percentage tear strength in a range of 45-60 MPa, no deformation in a range of 0.5% strain over a 8-24 hour period, a stress relaxation rate (N/s) in a range of 0.010-0.020, and a notch impact resistance at 23° C. of 16 kJ/m2 (DIN 53453).

An example method may include generating a first virtual model of teeth of a patient, generating a second model of orthodontic teeth movement based on the first model, generating a third model of forces to achieve the orthodontic teeth movement, and 3D-printing at least part of an aligner to fit over one or more of the teeth to apply at least part of the forces to at least one tooth.

The example method may further include fixing a divot anchor to a tooth of the patient, and placing the aligner over the divot anchor and over the teeth of the patient, wherein the aligner attaches to a divot of the divot anchor and applies a torque, a rotational force, a leverage, a push, a pull, or at least part of a full 3D control force to the tooth.

In the foregoing description, the invention has been described with reference to specific exemplary embodiments thereof. It will be apparent to those skilled in the art that a person understanding this invention may conceive of changes or other embodiments or variations, which utilize the principles of this invention without departing from the broader spirit and scope of the invention. The specification and drawings are, therefore, to be regarded in an illustrative rather than a restrictive sense.

The invention claimed is:

1. An orthodontic system, comprising:
an anchor independently attachable to a tooth of a patient, the anchor for applying a force to the tooth;
an aligner for fitting over the tooth, over the anchor, and over one or more other teeth of the patient, the aligner 3D-printed to contact the anchor and apply the force when worn by the patient;
a geometry of the aligner 3D-printed to apply a torque, a rotational force, a leverage, a push, a pull, or at least part of a full 3D control force to the anchor when the aligner is worn by the patient;
the geometry of the aligner 3D-printed to establish at least one space proximate to the tooth along a direction of movement caused by a force vector originating at the anchor, the at least one space to allow a movement of the tooth caused by the applied force;

at least one spacer 3D-printed as part of the aligner, the at least one spacer disposed within the confines of the aligner and positioned proximate to a side of the tooth to decrease a resistance of the tooth to the movement caused by the applied force; and the at least one spacer comprising a soft material 3D-printed as part of the aligner or comprising a suction member 3D-printed as part of the aligner to pull the tooth in the direction of the movement caused by the applied force at the anchor.

2. The orthodontic system of claim 1, wherein at least a part of the aligner comprises a 3D-printed material capable of an elastic strain recovery for applying the force to the anchor.

3. The orthodontic system of claim 1, wherein multiple anchors are each independently attachable to the tooth, and the aligner is 3D-printed to apply a different force vector to the tooth through a corresponding 3D-printed contact with each respective anchor of the multiple anchors.

4. The orthodontic system of claim 1, wherein the anchor further comprises a groove, a channel, a notch, a depression, a cavity, or a hole for securing a tab, a flange, a rib, a hook, an extension, a geometry, or a member of the aligner for applying an additional force to the tooth, wherein the force comprises one of a torque, a rotational force, a leverage, a push, a pull, or at least part of a full 3D control force.

5. The orthodontic system of claim 1, wherein at least one 3D-printed part of the aligner is constructed in an additive manufacturing process.

6. The orthodontic system of claim 1, further comprising a torque control feature of the aligner, the torque control feature comprising the at least one space adapted to be disposed between the aligner and at least one tooth, and the at least one spacer.

7. The orthodontic system of claim 6, further comprising a compressible material adapted to be disposed in the at least one space between the aligner and the at least one tooth.

8. The orthodontic system of claim 1, wherein the aligner comprises a plurality of 3D-printed materials each having a different modulus of elasticity (MOE) for applying a different force to a respective anchor via a corresponding 3D-printed geometry of the aligner.

9. The orthodontic system of claim 8, where the aligner comprises a first 3D-printed material with a first modulus of elasticity (MOE) for front teeth and a second 3D-printed material with a second modulus of elasticity (MOE) for back teeth.

10. The orthodontic system of claim 8, further comprising an additive combined with one 3D-printed material of the aligner, the one 3D-printed material associated with applying an individual force to the tooth via a respective anchor in contact with the one 3D-printed material of the aligner, the additive fading over a time interval assigned to the one 3D-printed material.

11. The orthodontic system of claim 1, wherein at least part of the aligner for applying a force through an anchor is 3D-printed in an additive manufacturing process selected from the group consisting of a FDM process, a SLS process, a direct pellets fused deposition process, a SLA process, a DLP process (modified SLA) a multi-jet photo cured polymer process, a multi jet fusion technology, and a CLIP process.

12. The orthodontic system of claim 1, further comprising a microchip and a sensor embedded in the aligner to detect a tooth movement or a changing angularity over a time interval or to verify each contact with an anchor.

13. The orthodontic system of claim 1, wherein the aligner comprises multiple thicknesses of a 3D-printed material, wherein a first thickness of the 3D-printed material applies a first force to a first anchor and a second thickness of the 3D-printed material applies a second force to a second anchor.

14. The orthodontic system of claim 1, further comprising a pigment or a coloring agent in the aligner formulated to match a color of the teeth or to match a color of an anchor.

15. The orthodontic system of claim 1, further comprising a polymeric coating on the aligner to reduce a surface porosity and to increase a surface smoothness of the aligner.

16. The orthodontic system of claim 1, wherein the at least one 3D-printed part of the aligner comprises a material having a hardness on a Shore D scale in a range of 40-90, an elasticity modulus in a range of 1000-1800 Mpa (ASTM 638-2010), a tensile strength at yield in a range of 40-70 Mpa (ASTM 638-2010), a percentage elongation at break in a range of 80-200% (ASTM 638-2010), a percentage tear strength in a range of 45-60 MPa (ASTM D 1938), no deformation in a range of 2% to 10% strain over a 8-24 hour period (ASTM 638-2010), a stress relaxation rate (N/s) in a range of 0.010-0.020 (ASTM D 2991), a notch impact resistance at 23° C. of 16 kJ/m$^2$ (DIN 53453); and wherein when measured by a nanoindentation tester (ASTM E2546) the material has an elastic (Young) modulus in a range of 600-2000 MPa, a hardness in a range of 40-160 Mpa, and a creep in a range of 120-400 nm.

* * * * *